US012156765B2

(12) United States Patent
Moehring et al.

(10) Patent No.: US 12,156,765 B2
(45) Date of Patent: Dec. 3, 2024

(54) METHODS AND DEVICES FOR MEMBRANE CHARACTERIZATION WITH ULTRASOUND AND OPTICAL ILLUMINATION

(71) Applicant: OtoNexus Medical Technologies, Inc., Bellevue, WA (US)

(72) Inventors: Mark A. Moehring, Seattle, WA (US); Daniel Kreindler, Foster City, CA (US); Charlie Corredor, Seattle, WA (US); Chad Jason MacDonald, Bothell, WA (US); Dar Bahatt, Foster City, CA (US)

(73) Assignee: OtoNexus Medical Technologies, Inc., Bellevue, WA (US)

( * ) Notice: Subject to any disclaimer, the term of this patent is extended or adjusted under 35 U.S.C. 154(b) by 0 days.

(21) Appl. No.: 17/218,731

(22) Filed: Mar. 31, 2021

(65) Prior Publication Data
US 2021/0236089 A1    Aug. 5, 2021

Related U.S. Application Data

(63) Continuation of application No. 16/591,910, filed on Oct. 3, 2019.
(Continued)

(51) Int. Cl.
*A61B 8/00* (2006.01)
*A61B 1/227* (2006.01)
(Continued)

(52) U.S. Cl.
CPC .......... *A61B 8/4416* (2013.01); *A61B 1/2275* (2013.01); *A61B 1/32* (2013.01);
(Continued)

(58) Field of Classification Search
CPC ....... A61B 8/4416; A61B 8/08; A61B 8/4494; A61B 8/12; A61B 1/2275; A61B 5/6817
See application file for complete search history.

(56) References Cited

U.S. PATENT DOCUMENTS

| 4,335,713 A | 6/1982 | Komiya |
| 5,345,926 A | 9/1994 | Chikama |

(Continued)

FOREIGN PATENT DOCUMENTS

| CN | 105380677 A | 3/2016 |
| JP | 2005519666 A | 7/2005 |

(Continued)

OTHER PUBLICATIONS

PCT/US2019/054571 International Search Report dated Jan. 29, 2020.
(Continued)

*Primary Examiner* — Jason M Ip
(74) *Attorney, Agent, or Firm* — Wilson Sonsini Goodrich & Rosati

(57) ABSTRACT

A device for measuring reflected ultrasound and optical signals may include: an optical source; an optical assembly comprising at least one lens, configured to focus reflected optical illumination from a target onto a detector; and an ultrasound transducer aligned to transmit and receive ultrasound radiation co-axially with the reflected optical illumination and wherein the ultrasound transducer at least partially obstructs a path of the reflected optical illumination. An obstruction may be distant from a focal spot of the optical assembly. The device for measuring reflected ultrasound and optical signals may be particularly useful for characterizing fluid behind an ear drum to diagnose otitis media.

27 Claims, 21 Drawing Sheets

Related U.S. Application Data

(60) Provisional application No. 62/740,862, filed on Oct. 3, 2018.

(51) Int. Cl.
*A61B 1/32* (2006.01)
*A61B 8/08* (2006.01)
*A61B 8/12* (2006.01)

(52) U.S. Cl.
CPC .................. *A61B 8/08* (2013.01); *A61B 8/12* (2013.01); *A61B 8/4494* (2013.01)

(56) References Cited

U.S. PATENT DOCUMENTS

| | | | |
|---|---|---|---|
| 5,363,839 A * | 11/1994 | Lankford | ............. A61B 1/2275 600/112 |
| 6,789,426 B2 | 9/2004 | Yaralioglu et al. | |
| 7,321,181 B2 | 1/2008 | Khuri-Yakub et al. | |
| 7,545,075 B2 | 6/2009 | Huang et al. | |
| 8,531,919 B2 | 9/2013 | Cheng et al. | |
| 8,858,425 B2 | 10/2014 | Farr et al. | |
| 8,932,223 B2 | 1/2015 | Emelianov et al. | |
| 9,867,528 B1 | 1/2018 | Boppart et al. | |
| 9,925,561 B2 | 3/2018 | Emadi et al. | |
| 10,660,604 B2 | 5/2020 | Moehring et al. | |
| 10,675,001 B2 | 6/2020 | Moehring et al. | |
| 2003/0139673 A1 | 7/2003 | Vivenzio et al. | |
| 2004/0073118 A1 | 4/2004 | Peszynski et al. | |
| 2005/0027168 A1 * | 2/2005 | Strom | .................... A61B 1/227 600/200 |
| 2007/0129632 A1 | 6/2007 | Voie et al. | |
| 2008/0045838 A1 | 2/2008 | Hyuga | |
| 2008/0208006 A1 | 8/2008 | Farr | |
| 2009/0306517 A1 | 12/2009 | Burns | |
| 2010/0173437 A1 | 7/2010 | Wygant et al. | |
| 2010/0191144 A1 | 7/2010 | Zoth et al. | |
| 2010/0198009 A1 | 8/2010 | Farr et al. | |
| 2010/0217102 A1 | 8/2010 | LeBoeuf et al. | |
| 2011/0257521 A1 | 10/2011 | Fraden | |
| 2012/0068571 A1 | 3/2012 | Chen | |
| 2012/0179187 A1 * | 7/2012 | Loushin | ................ A61F 11/202 606/185 |
| 2012/0271170 A1 | 10/2012 | Emelianov et al. | |
| 2013/0027515 A1 | 1/2013 | Vinther et al. | |
| 2014/0265720 A1 | 9/2014 | El-Gamal et al. | |
| 2014/0276248 A1 | 9/2014 | Hall et al. | |
| 2015/0065803 A1 * | 3/2015 | Douglas | ................... G06T 7/143 600/200 |
| 2015/0112181 A1 | 4/2015 | Yoon et al. | |
| 2015/0133732 A1 | 5/2015 | Goldfain | |
| 2015/0229236 A1 | 8/2015 | Tian et al. | |
| 2015/0272445 A1 | 10/2015 | Rozental et al. | |
| 2016/0143519 A1 | 5/2016 | Harris | |
| 2016/0199030 A1 | 7/2016 | Patil et al. | |
| 2016/0203809 A1 | 7/2016 | Brock-Fisher et al. | |
| 2016/0282312 A1 | 9/2016 | Cable et al. | |
| 2017/0014053 A1 * | 1/2017 | Moehring | ................ A61B 8/12 |
| 2017/0119237 A1 | 5/2017 | Bedard et al. | |
| 2017/0171437 A1 * | 6/2017 | Xiao | ................... H04N 5/2253 |
| 2017/0232474 A1 | 8/2017 | Oralkan et al. | |
| 2017/0360397 A1 | 12/2017 | Rothberg et al. | |
| 2018/0014811 A1 | 1/2018 | Sonnenschein | |
| 2018/0125346 A1 | 5/2018 | Shelton et al. | |
| 2018/0168440 A1 | 6/2018 | Das et al. | |
| 2018/0185008 A1 | 7/2018 | Andersen et al. | |
| 2018/0310917 A1 | 11/2018 | Moehring et al. | |
| 2020/0107813 A1 | 4/2020 | Moehring et al. | |
| 2024/0016377 A1 | 1/2024 | Alleman et al. | |

FOREIGN PATENT DOCUMENTS

| | | |
|---|---|---|
| JP | 2006345903 A | 12/2006 |
| WO | WO-2020072822 A1 | 4/2020 |
| WO | WO-2020206401 A1 | 10/2020 |
| WO | WO-2022272136 A1 | 12/2022 |

OTHER PUBLICATIONS

European search report and opinion dated May 20, 2022 for EP Application No. 19868783.2.
U.S. Appl. No. 16/591,910 Office Action dated May 2, 2023.
U.S. Appl. No. 16/591,910 Office Action dated Nov. 7, 2023.
PCT/US2022/035003 International Search Report and Written Opinion dated Nov. 1, 2022.
U.S. Appl. No. 16/591,910 Notice of Allowance dated Apr. 25, 2024.

* cited by examiner

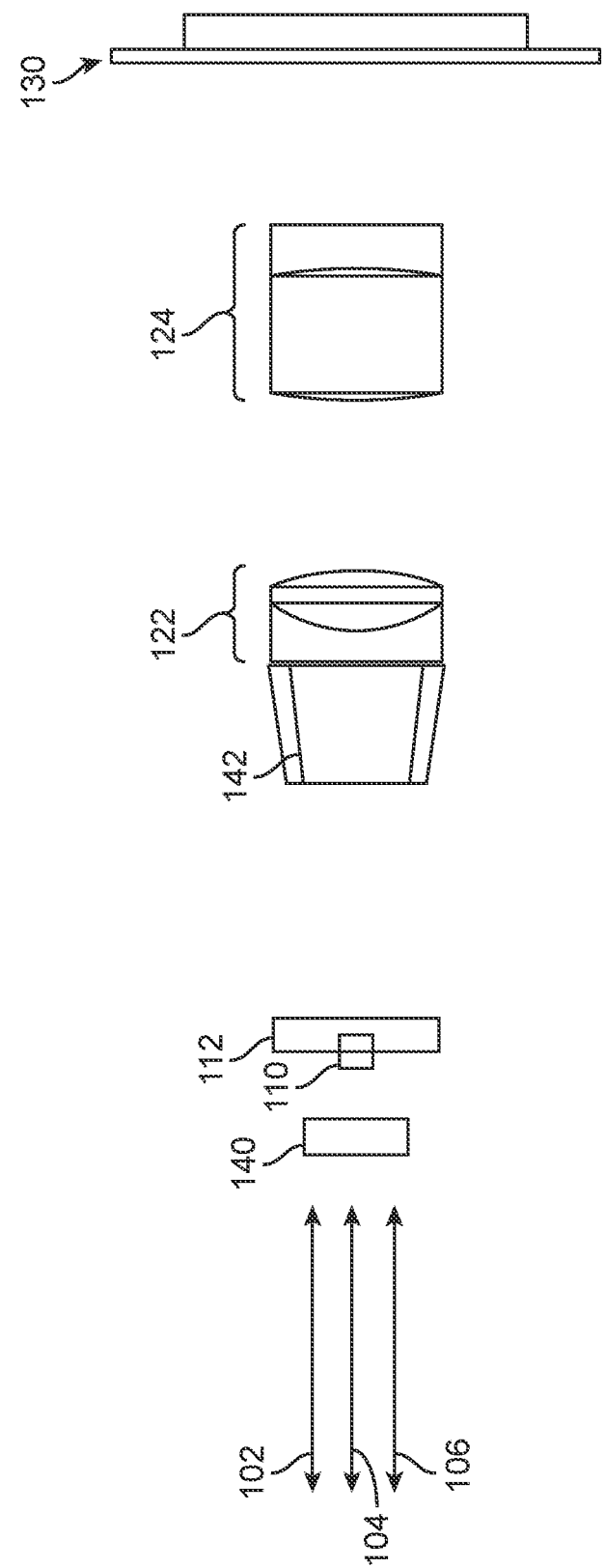

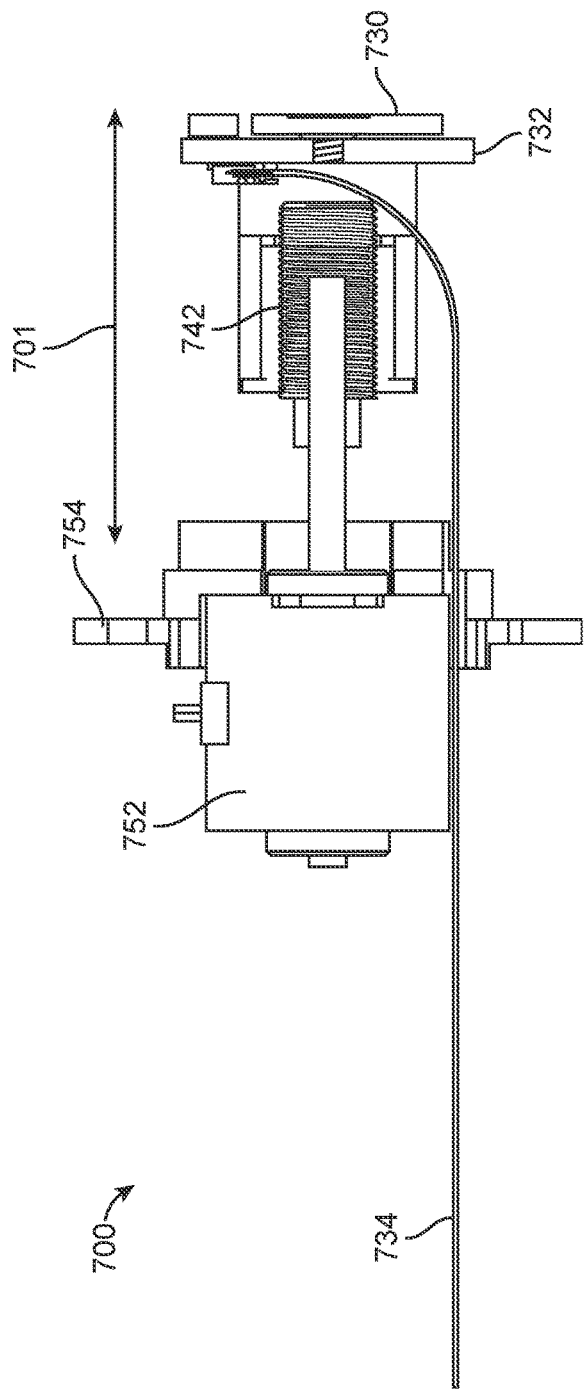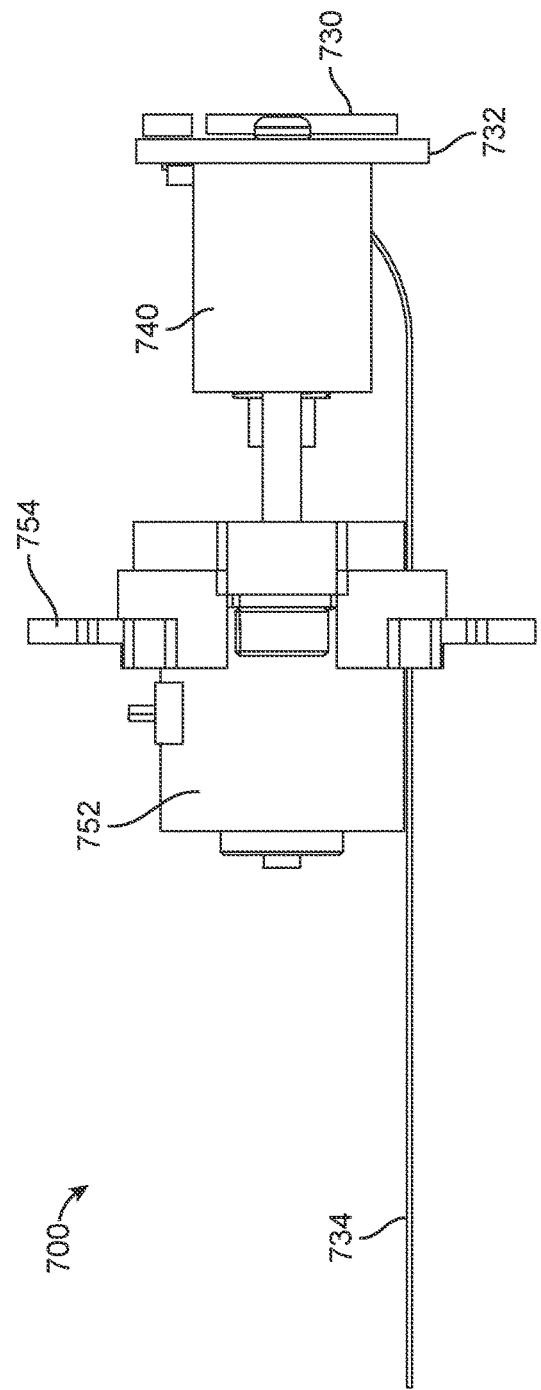

METHODS AND DEVICES FOR MEMBRANE CHARACTERIZATION WITH ULTRASOUND AND OPTICAL ILLUMINATION

CROSS-REFERENCE

This is a continuation of U.S. patent application Ser. No. 16/591,910 filed Oct. 3, 2019, which claims the benefit of U.S. Provisional Patent Application Ser. No. 62/740,862 filed on Oct. 3, 2018, both of which are hereby incorporated by reference in their entireties.

BACKGROUND

Acute otitis media (AOM) is an inflammatory process in the middle ear and is the most common clinical condition seen by pediatricians in children fifteen years and younger. AOM is generally associated with the presence of a middle ear effusion and is considered a middle ear inflammation. Complications of undiagnosed AOM can include hearing loss. Left untreated in children, recurrent AOM can also lead to delays in the development of speech and language skills.

The likelihood of obtaining an accurate diagnosis using existing non-invasive methods may be no better than 50%. Further, existing non-invasive methods may only be useful in identifying the presence of an effusion, and they often provide no information regarding the type of effusion. Because of the risks associated with undiagnosed AOM and the recognized unreliability of existing diagnostic tests, patients are often prescribed antibiotics, which may be ineffective in treating viral effusion. In addition to the increased cost burden of unnecessary antibiotic treatment, the patients are exposed to the side effects of antibiotics and the attendant and significant risk of developing antibiotic resistance.

The following commonly owned references may be of interest: U.S. Patent Publication 2018/0310917 and U.S. Patent Publication 2017/0014053, each of which is incorporated by reference in their entireties.

The following reference may be of interest: U.S. Pat. No. 5,345,926.

SUMMARY

Devices and methods described herein may improve upon existing non-invasive techniques by measuring ultrasound data reflected from a biological membrane coincident with a pneumatic excitation. The size of a diagnostic target may be small, and ultrasound is not visible to a human eye. An optical source and detection system may be provided. The optical source and detection system may facilitate alignment of the ultrasound beam. As the size of a biological lumen may be small, the optical source and detection system may be space efficient. The present disclosure provides improvements to delivering optical illumination to a target. The present disclosure provides improvements receiving optical illumination from a target in the presence of an obstruction.

In an aspect, the present disclosure provides a speculum operable to be disposed within an ear of a subject. The speculum may comprise: a housing comprising a light conducting element, wherein a transmitted optical illumination is conducted by total internal reflection via the light conducting element, wherein the housing has a lumen therewithin, and wherein the housing is configured to allow a reflected optical illumination to propagate therethrough; and an obstruction disposed within the lumen proximate a distal end of the housing, the obstruction at least partially obstructing the reflected optical illumination, wherein the obstruction comprises a largest dimension less than 75% of a smallest diameter of the lumen.

In some embodiments, the obstruction comprises an ultrasound transducer. In some embodiments, ultrasound transducer is centered relative to a distal end of the housing. In some embodiments, a transmission axis of the ultrasound transducer is coaxial with an axis of symmetry of the housing. In some embodiments, the housing is frustoconical in shape. In some embodiments, a transmission axis of the ultrasound transducer is coaxial with an optical path of the reflected optical illumination. In some embodiments, the largest dimension is a diameter. In some embodiments, the diameter is within a range within 20% to 60% of the smallest diameter of the lumen.

In some embodiments, the light conducting element comprises one or more optic fibers adjacent the housing. In some embodiments, a portion of the housing is configured to transmit light by total internal reflection such that the portion of the housing is the light conducting element. In some embodiments, the housing comprises a light conducting core. In some embodiments, the housing comprises an opaque shell. In some embodiments, the speculum is disposable.

In some embodiments, the speculum is removably attachable to an otoscope. In some embodiments, the speculum is removably connected to a device for measuring reflected optical and ultrasound signals. In some embodiments, the speculum when connected to the device is axially aligned with a focal axis of an optical assembly. In some embodiments, the optical assembly comprises a focus within a range from 12-25 mm from a distal tip of the otoscope. In some embodiments, the optical assembly comprises a depth of field of greater than 0.5 mm at a distance 12-25 mm from the distal tip of the otoscope.

In some embodiments, the optical assembly comprises at least one lens. In some embodiments, the at least one lens is a relay lens. In some embodiments, the relay lens comprises one or more concave, convex, planoconcave, or planoconvex lenses. In some embodiments, relay lens comprises one or more achromatic doublets. In some embodiments, the relay lens comprises one or more gradient-index of refraction lenses. In some embodiments, the relay lens comprises a rod lens relay. In some embodiments, the at least one lens comprises at least two lenses which form a first telescope.

In some embodiments, the ultrasound transducer is mounted upon a transducer mount assembly. In some embodiments, the transducer mount assembly comprises one or more apertures to allow transmission of a pneumatic excitation around the ultrasound transducer. In some embodiments, the transducer mount assembly is press fit into the housing of the speculum. In some embodiments, a distal end of the transducer mount assembly is operably coupled to a transparent plate. In some embodiments, the transparent plate comprises the ultrasound transducer mounted on a surface thereof. In some embodiments, a portion of the transducer mount assembly is electrically conducting. In some embodiments, the ultrasound transducer comprises a largest dimension of less than 2 mm. In some embodiments, a metal shield is disposed around the ultrasound transducer, wherein the metal shield is radially displaced away from a transmission axis of the ultrasound transducer. In some embodiments, the speculum comprises a pressure gauge configured to measure an internal pressure within the speculum.

In another aspect, the present disclosure provides device for measuring reflected optical and ultrasound signals. The device may comprise: an optical source; an optical assembly comprising at least one lens, configured to focus reflected optical illumination from a target onto a detector; and an ultrasound transducer aligned to transmit and receive ultrasound radiation co-axially with the reflected optical illumination and wherein the ultrasound transducer at least partially obstructs a path of the reflected optical illumination; wherein the optical assembly comprises a focus within a range from 12-25 mm from a distal tip of the otoscope and a depth of field of greater than 0.5 mm at a distance 12-25 mm from the distal tip of the otoscope.

In some embodiments, the device comprises the speculum any aspect or embodiment. In some embodiments, the ultrasound transducer is centered relative to a focal axis of the optical assembly. In some embodiments, a transmission axis of the ultrasound transducer is coaxial with a focal axis of the optical assembly. In some embodiments, a transmission axis of the ultrasound transducer is coaxial with an optical path of the reflected optical illumination. In some embodiments, the ultrasound transducer comprises a relative size of 20%-50% of an aperture of the optical assembly. In some embodiments, the optical source comprises one or more optic fibers.

In some embodiments, the optical source is configured to deliver light to a speculum. In some embodiments, a portion of the speculum is configured to transmit light by total internal reflection. In some embodiments, the speculum comprises a light conducting core. In some embodiments, the speculum comprises an opaque shell. In some embodiments, the speculum is disposable. In some embodiments, the device is an otoscope. In some embodiments, the speculum is removably connected to the device.

In some embodiments, the speculum when connected to the device is axially aligned with a focal axis of an optical assembly. In some embodiments, the optical assembly comprises at least one lens. In some embodiments, the at least one lens is a relay lens. In some embodiments, the relay lens comprises one or more concave, convex, planoconcave, or planoconvex lenses. In some embodiments, the relay lens comprises one or more achromatic doublets. In some embodiments, the relay lens comprises one or more gradient-index of refraction lenses. In some embodiments, the relay lens comprises a rod lens relay. In some embodiments, the at least one lens comprises at least two lenses which form a first telescope.

In some embodiments, the ultrasound transducer is mounted upon a transducer mount assembly. In some embodiments, the transducer mount assembly comprises one or more apertures to allow transmission of a pneumatic excitation around the ultrasound transducer. In some embodiments, the transducer mount assembly is press fit into the housing of a speculum. In some embodiments, a distal end of the transducer mount assembly is operably coupled to a transparent plate. In some embodiments, the transparent plate comprises the ultrasound transducer mounted on a surface thereof. In some embodiments, a portion of the transducer mount assembly is electrically conducting. In some embodiments, the ultrasound transducer comprises a largest dimension of less than 2 mm. In some embodiments, a metal shield is disposed around the ultrasound transducer, wherein the metal shield is radially displaced away from a transmission axis of the ultrasound transducer. In some embodiments, the device further comprises a pressure gauge configured to measure an internal pressure within the speculum In another aspect, the present disclosure provides a method of using an otoscope. The method may comprise: directing optical illumination toward a target; directing pneumatic excitation toward the target; directing ultrasonic toward the target, wherein the ultrasonic is copropagating with the optical illumination; receiving a reflected optical illumination from the target at a detector; measuring a response of the target to the pneumatic excitation in the reflected ultrasound; and determining a state or condition of a subject based on the reflected optical illumination and the response.

In some embodiments, the method further comprises providing the device of any aspect or embodiment. In some embodiments, the method further comprises providing the speculum of any aspect or embodiment.

In another aspect, the present disclosure provides a speculum operable to be disposed within an ear of a subject. The speculum may comprise: a frustoconical housing configured to be disposed within an ear canal and comprising a lumen; one or more optic fibers adjacent the frustoconical housing and extending from a proximal opening to a distal tip of the frustoconical housing; and an ultrasound transducer mounted within the frustoconical housing proximate the distal tip and aligned to transmit and receive ultrasound radiation co-axially with a reflected optical illumination, and wherein the ultrasound transducer at least partially obstructs a path of the reflected optical illumination.

In some embodiments, the speculum further comprises the speculum any aspect or embodiment, wherein the obstruction comprises at least the ultrasound transducer and wherein the one or more optic fibers comprises the light conducting element. In some embodiments, the speculum is removably attached to the device of any aspect or embodiment. In some embodiments, the ultrasound transducer is centered relative to a distal end of the housing. In some embodiments, the ultrasound transducer is coaxial with the housing. In some embodiments, the speculum comprises a quick release fitting. In some embodiments, a diameter of the ultrasound transducer is less than 50% of a lumen of the housing open at a distal end of the housing. In some embodiments, the speculum is disposable.

In another aspect, the present disclosure provides a speculum operable to be disposed within an ear of a subject. The speculum may comprise: a frustoconical housing configured to be disposed within an ear canal and configured to transmit light by total internal reflection; an ultrasound transducer mounted within the frustoconical housing proximate a distal tip of the frustoconical housing, wherein the ultrasound transducer is sufficiently small to allow passage of reflected light through a lumen of the housing.

In some embodiments, the speculum further comprises the speculum of any aspect or embodiment, wherein the obstruction comprises at least the ultrasound transducer and wherein the housing comprises the light conducting element. In some embodiments, the speculum is removably attached to the device of any aspect or embodiment. In some embodiments, the ultrasound transducer is centered relative to a distal end of the housing. In some embodiments, the ultrasound transducer is coaxial with the housing. In some embodiments, the speculum is disposable.

In another aspect, the present disclosure provides an otoscope. The otoscope may comprise: an interface to releasably couple to a speculum; an optical assembly comprising at least one lens with an aperture, wherein the optical assembly comprises a focus within a range from 12-25 mm from a distal tip of the otoscope and a depth of field of greater than 0.5 mm at a distance 12-25 mm from the distal tip of the otoscope; a central obstruction along an optical path from the optical assembly to a target, wherein the central obstruction has a diameter less than 50% of the aperture. In some embodiments, the speculum further comprises the speculum of any aspect or embodiment.

In another aspect, the present disclosure provides an otoscope. The otoscope may comprise: a speculum and having a lumen therewithin and comprising a light conducting element, wherein a transmitted optical illumination is conducted by total internal reflection by the light conducting element, and wherein a reflected optical illumination is propagated through the lumen of the speculum; a central obstruction disposed within the speculum proximate the distal end, the central obstruction at least partially obstructing the reflected optical illumination; and an optical assembly comprising at least one lens having a focal length which is longer than the distance from the lens to the central obstruction. In some embodiments, the speculum further comprises the speculum of any aspect or embodiment.

In another aspect, the present disclosure provides a method of using an optical and ultrasonic device. The method may comprise: directing optical illumination toward a target; directing ultrasound toward the target; receiving reflected ultrasound from the target; and adjusting a focus of the optical illumination based on the received reflected ultrasound, wherein the adjusting is performed substantially in real time. In some embodiments, the method further comprises calculating an image crispness, calculating a derivative of the image crispness, and adjusting the focus based on the image crispness.

In another aspect, the present disclosure provides a method of manufacturing a speculum operable to be disposed within an ear. The method may comprise: mounting an ultrasound transducer on a substrate; mounting the substrate on a support comprising an electrically conducting portion, wherein the support has a pneumatically clear path when the support is mounted; and fitting the support within a lumen of the speculum, wherein the transducer is centered within the lumen of the speculum, wherein the speculum has an optically clear path when the transducer is within the lumen.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 1 is a side section view of an optical assembly for measuring optical and ultrasound signals, in accordance with some embodiments.

FIG. 7A is a side cross section view of an example detector assembly, in accordance with some embodiments.

FIG. 7B is a side view of the detector assembly of FIG. 7A, in accordance with some embodiments.

DETAILED DESCRIPTION

Figure 2A:
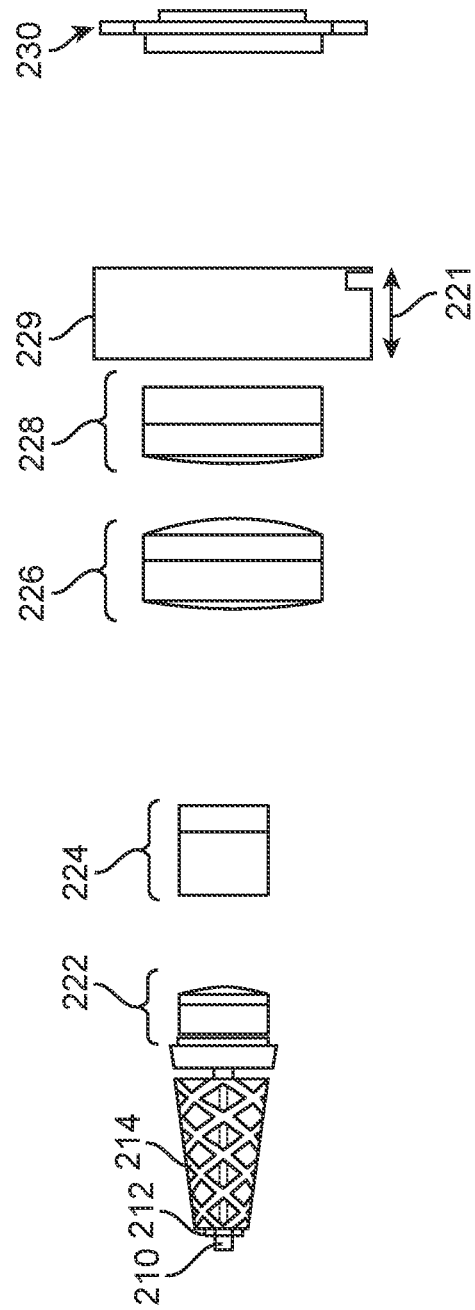
FIG. 2A is a side section view of another optical assembly for measuring optical and ultrasound signals, in accordance with some embodiments.

The devices, otoscopes, specula, and methods of use and manufacture thereof as disclosed herein may address issues related to devices for measuring optical and ultrasound information. Embodiments of the present disclosure may improve upon the delivery of light and/or collection of light from a biological membrane, which may be characterized simultaneously with ultrasound excitation. The devices, otoscopes, specula, and methods of use and manufacture thereof as disclosed herein may address difficulties in the field with regard to the alignment of device for measuring reflected ultrasound signals. In some case, present disclosure addresses issues in the field of otoscopy.

For example, surface characterization using an analysis of reflected ultrasound in the presence of a pneumatic excitation may be improved if the delivery optical illumination, pneumatic excitation, and ultrasound signal is space efficient. For example, surface characterization using an analysis of reflected ultrasound in the presence of a pneumatic excitation may be improved if the measurement of reflected ultrasound signal and reflected optical illumination is space efficient.

For example, surface characterization using an analysis of reflected ultrasound in the presence of a pneumatic excitation may be improved if the ultrasound is directed at the surface at an angle that will result in ultrasound signal being returned to the transducer. Because ultrasound excitation is not visible to an eye, particularly the eye of a device operator, alignment of the ultrasound may be non-trivial. In one solution, a light source may be directed toward the surface to allow a user to better adjust an alignment of the device. The light source may be substantially aligned with the ultrasound propagation. In an ear, a user may align a light source within an ear canal to reflect light off of the tympanic membrane. A good reflection may result in a "cone of light." However, because a user may not look directly through the center of the lens and/or because a transducer may block the reflected light, the ultrasound and the light may not be propagating in the same direction.

The devices, otoscopes, specula, and methods of use and manufacture thereof as disclosed herein may be used in combination with for example devices and methods to characterize a ductile membrane, surface, and sub-surface properties such as those described in commonly owned U.S. Patent Publication 2018/0310917 and U.S. Patent Publication 2017/0014053, each of which is incorporated by reference in their entireties.

The devices, otoscopes, specula, and methods of use and manufacture thereof as disclosed herein may be used to characterize a number of biological tissues to provide a variety of diagnostic information. A biological tissue may comprise a patient organ. A speculum may be disposed within a bodily cavity to characterize a patient tissue. A patient organ or bodily cavity may comprise for example: a muscle, a tendon, a ligament, a mouth, a tongue, a pharynx, an esophagus, a stomach, an intestine, an anus, a liver, a gallbladder, a pancreas, a nose, a larynx, a trachea, lungs, a kidneys, a bladder, a urethra, a uterus, a vagina, an ovary, a testicle, a prostate, a heart, an artery, a vein, a spleen, a gland, a brain, a spinal cord, a nerve, etc, to name a few.

The devices, otoscopes, specula, and methods of use and manufacture thereof as disclosed herein may be used to characterize a tympanic membrane. For example, a membrane may be characterized to determine a condition of an ear, such as acute otitis media (AOM). A characterization that an ear exhibits AOM may include detection of the presence of effusion and characterization of the type of effusion as one of serous, mucoid, purulent, or combinations of these. In AOM, the middle ear effusion (MEE) may be induced by infective agents and may be thin or serous with viral infection and thicker and purulent with bacterial infection. Accordingly, determining various properties of a fluid adjacent a tympanic membrane may provide information which may be used to characterize a membrane.

The devices, otoscopes, specula, and methods of use and manufacture thereof as disclosed herein may be used to characterize a food item. For example, the pneumatic excitation may apply an impulsive pressure to the surface of a food item such as a vegetable, a fruit, a meat, a dairy, a grain, etc., and the ultrasound energy may applied to the food item to measure the time dependent surface response of the food item. For example, the surface response of a fruit or vegetable may be used to determine an elasticity or other physical property which may be correlated to the ripeness of the fruit or vegetable. For example, a presence of mold on a surface of a bread item may change the surface response of the crust. For example, a surface property of a yogurt or a cheese may be determined to assess firmness of the cultured milk product. For example, a meat or a meat product surface response may relate to a degree to which it has been cooled. For example, the food item may be placed into a holder and the surface excited with a puff of gas such as air, the surface deflection response estimating ripeness or other property. For example, the excitation may be a gas which may be delivered at a supersonic velocity and/or at a glancing angle to the surface of the food item, or one or more food items may be placed into a chamber which has a variable pressure to measure a low frequency surface response to pressure, such as deflection vs. pressure. For example, the excitation may be applied to one surface and the response measured on a different surface of the same item, such as the measurement of a propagating surface wave or a shear wave which travels through the item being characterized.

The devices, otoscopes, specula, and methods of use and manufacture thereof as disclosed herein may be used to characterize an industrial process. For example, the pneumatic excitation may apply an impulsive pressure to the surface of a manufactured part such as to determine the consistency of a viscous fluid such as a lubricant, and the ultrasound energy may applied to the part to measure the time dependent surface response of the viscous fluid, to determine an elasticity or other physical property which may be correlated to quality of the lubricant. Other industrial examples may include range finding applications, ultrasonic transit-time gas flow meters for metering dynamic gas flows, anemometry applications, and various other ultrasound-based sensing applications.

Reference will now be made in detail to various embodiments, examples of which are illustrated in the accompanying drawings. In the following detailed description, numerous specific details are set forth in order to provide a thorough understanding of the present disclosure and the described embodiments. However, the embodiments of the present disclosure are optionally practiced without these specific details. In other instances, well-known methods, procedures, components, and circuits have not been described in detail so as not to unnecessarily obscure aspects of the embodiments. In the drawings, like reference numbers designate like or similar steps or components.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range.

As used herein, the terms "comprises", "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "subject" and "patient" are used interchangeably. As used herein, the terms "subject" and "subjects" refers to an animal (e.g., birds, reptiles, and mammals), a mammal including a primate (e.g., a monkey, chimpanzee, and a human) and a non-primate (e.g., a camel, donkey, zebra, cow, pig, horse, cat, dog, rat, and mouse). In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100.

FIG. 1 is a side section view of an optical assembly for measuring optical and ultrasound signals, in accordance with some embodiments. As shown, the optical assembly comprises first lens 122 and second lens 124. The first and second lens may comprise focal axes which are substantially co-axially aligned. FIG. 1 illustrates focal axis 102 of first lens 122 and second lens 124. As shown, the device comprises ultrasound transducer 110 on plate 112. Ultrasound transducer 110 may be configured to transmit ultrasound signal and/or receive ultrasound signal along ultrasound axis 104. Ultrasound transducer 110 may be located on focal axis 102. In some cases, ultrasound transducer 110 may obstruct light propagated along 102. Plate 112 may be located on focal axis 102. Plate 112 may be transparent or partially transparent to light propagated along focal axis 102. In some cases, a device may comprise a detector 130. The detector may be located along a focal axis 102. The detector may be sized and shaped to receive light collected by first lens 122 and second 124. The detector may be sensitive to a wavelength range propagated along optical path 102. In some cases, a device may comprise an optical source, not shown. In other cases, a device may not comprise an optical source. In some cases, light propagated along focal axis 102 may comprise light scattered along focal axis 102. In some cases, a focal axis 102 and an ultrasound axis 104 may also be co-linear with pneumatic axis 106. A pneumatic perturbation may be propagated along axis 106.

An optical assembly as described herein may comprise one or more optical components, such components may include one or more lens, one or more mirrors, one or more beam splitters, one or more prisms, one or more filters, one or more polarizers, one or more diffusers, one or more apertures, one or beam tubes, one or more waveplates, or other optical components. In some cases, the optical assembly comprises beam tube 142. In some cases, the optical assembly comprises exit aperture 140.

In some cases, the first lens 122 and the second lens 124 may function together to collect and/or transmit light. In some cases, lens 122 and lens 124 comprise an optical telescope. In some cases, an optical telescope is a reflecting telescope, a refracting telescope, or a combination thereof. Lenses as described herein may comprise a focal length and an aperture. The magnification of a telescope may be related as a ratio of the first lens 122 and the second lens 124. As the magnification increase, a field of view may decrease. Similarly, as the aperture of the lens increases, the field of view may increase. The focal length may also affect the depth of focus of the optical assembly. For example, a longer focal length may result in longer depth of field. The focal lengths and apertures may be adjusted to image a target a distance from the first and second lenses. Similarly, the focal lengths and apertures may be adjusted to image around a central obstruction. An obstruction located along the focal axis may result in spatial aberration of the image. The further the obstruction from the focal zone, the less apparent the spatial aberration due to the central obstruction. As the depth of focus increases, the closer the obstruction to the focal zone. Size may also be limited by the intended use and access to the target region. For example, if the target is within a bodily lumen, a small diameter and smaller aperture lens may be desirable.

Lenses as described herein may comprise individual lenses or compound lenses. A compound lens may be a relay lens. A relay lens may comprise one or more pairs of optical substrates with differing optical properties, for example, one substrate may be a flint glass and one substrate may be Schott glass. A relay lens may comprise one of more individual lenses. A relay lens may comprise one or more achromatic doublets. An achromatic doublet may comprise low chromatic aberration. In some cases, the relay lens comprises one or more gradient-index of refraction lenses. In some case, the relay lens comprises a rod lens relay. While a first lens 122 and second les 124 are shown, an optical assembly may comprise additional lenses. For example, third and fourth lens and or a relay lens may function as an "erector" (e.g. the lenses may invert the image, which may be inverted by a refracting telescope).

Lenses as described herein may comprise one or more optical substrates. The optical substrates may include glasses and/or crystals. For example, an optical substrate disclosed herein may comprise a silicate glass, a sapphire, a quartz, etc.

A device as described herein may comprise an ultrasound transducer. An ultrasound transducer may be a capacitive micromachined ultrasound transducer. In some cases, an ultrasound transducer may be a piezoelectric transducer. An ultrasound transducer may transmit ultrasound radiation. An ultrasound transducer may be configured to receive ultrasound radiation. In some cases, a device may comprise driving circuitry. A driving circuitry may provide an electric waveform to the transducer which may transmit a waveform in response to the waveform. In some cases, a transducer may receive ultrasound radiation and may convert the received radiation to an electric waveform. The received electric waveform may be converted to a digital signal and/or stored by a digital processing device as disclosed elsewhere herein.

The ultrasound transducer may typically be small. For example, the ultrasound transducer may be configured to fit within a bodily lumen of a subject. The bodily lumen may be an ear canal. The ultrasound transducer may also be configured to allow light to propagate co-axially with the ultrasound. As the ultrasound transducer may impede transmission of light. A smaller transducer may result in an image with less aberration. The ultrasound transducer may comprise an active area with a diameter of less than 5 millimeter (mm), less than 2 mm, less than 1 mm, or less. The ultrasound transducer may comprise an active area with a diameter between 2 mm and 0.5 mm. The ultrasound transducer may comprise an active area between 1.5 mm and 0.5 mm. The ultrasound transducer may comprise a housing or base with a largest dimension of less than 5 millimeter (mm), less than 2 mm, less than 1 mm, or less.

The ultrasound transducer may be configured to transmit ultrasound signal within a specified band. For example, the ultrasound transducer may transmit ultrasound with a range from 0.1 Megahertz (MHz) to 10 MHz, from 1 MHz to 2 MHZ, or from 1.2 MHz to 1.8 MHz. In an example, the ultrasound transducer may have an angular beam spread between 10 and 20 degrees, within a 1.2 to 1.8 MHz bandwidth and for an edge length between 0.6 and 1.0 mm.

Ultrasound transducers 110, 210, 210, 410, and 510 may comprise embodiments, variations, or examples of any ultrasound transducer disclosed herein.

The ultrasound transducer may be mounted on plate 112. The plate may be at partially transparent to light propagated along focal axis 102. Plate 112 may be fractionally transparent. For example, the substrate may be 95% transparent to light propagated along path 102. For example, the substrate may be 85%, 75%, 50%, or less transparent to light propagated along path 102. For example, the substrate may comprise portions which are substantially transparent and other sections which are opaque. For example, the plate may be transparent to some wavelengths and absorbing for others. The plate may function as a chromatic filter. A plate may comprise one or more coatings which may affect a transparency of the substrate. Plate 112 may comprise a glass substrate, a quartz substrate, etc.

In some cases, the optical assembly may comprise detector 140. The detector may be a two-dimensional detector. A detector may be a CCD, a CMOS, a photodiode, a photodiode array, a thermal sensor, an optical sensor, etc. The detector may be sensitive to light within an optical spectrum. For example, the detector may be sensitive to at least light within a range from 400 to 800 nm, from 200 to 1000 nm, from 200 to 2500 nm, or wider. The detector may be operatively connected to a digital processing device, as described elsewhere herein. In some cases, the detector may form images from the received optical signal. The digital processing device may perform one or more storage, analysis, and/or image processing functions. In some cases, the images may be transmitted to a display. The display may be on-board the device or external to the device.

In embodiments which do not have detector, a user eye may not be perfectly aligned with a transmission axis of the ultrasound energy. This may not be ideal in cases where a user manually aligns a device with a target. If a user eye is not aligned with a transmission axis of the ultrasound, the ultrasound may be incorrectly pointed. A detector mounted within the device may center a focal axis along an ultrasound transmission axis. A detector mounted within the device may improve alignment of ultrasound and optical excitation on a target. For example, a detector mounted and centered on a focal axis of the optical assembly may be used as a reference and/or may be a sufficient reference for an axis of propagation of the ultrasound excitation. The ultrasound, which may be co-axial with the focal axis, may be aimed by putting the target at the center of the detected optical image. An optical image may be used as a surrogate for the ultrasound propagation. The optical image may be used in addition to aligning for an amplitude of the reflected ultrasound signal. An alignment aid on a display visible to a user may further aid in alignment of the ultrasound excitation. As ultrasound excitation is not visible to a user, improved alignment may be important.

FIG. 2A is a side section view of another optical assembly for measuring optical and ultrasound signals, in accordance with some embodiments. FIG. 2A illustrates an optical assembly for measuring optical and ultrasound signal comprising a pair of telescopes, in accordance with some embodiments. As shown, the optical assembly comprises first lens 222, second lens 224, third lens 226, fourth lens 228, and fifth lens 229. The lenses may comprise focal axes which are substantially co-axially aligned. As shown, the device comprises ultrasound transducer 210 on plate 212. Ultrasound transducer 210 may be configured to transmit ultrasound signal and/or receive ultrasound signal along an ultrasound axis. Ultrasound transducer 210 may be located on a focal axis of the optical assembly. For example, an axis of t the emitted ultrasound beam from the ultrasound transducer may be an axis of ultrasound propagation. An axis of ultrasound propagation may be co-axial with the focal axis. In some cases, ultrasound transducer 210 may obstruct light propagated along a focal axis of the optical assembly. Plate 212 may be located on a focal axis of the assembly. Plate 212 may be transparent or partially transparent to light propagated along a focal axis of the device. A plate may be mounted on a mount assembly 214. Ultrasound transducer 210 may comprise an embodiment, variation, or example of a transducer disclosed herein.

In some cases, a device may comprise imaging plane 230. In some cases, the imaging plane may be at the surface of the detector. In some cases, the imaging plane may be at a user eye. The detector may be located along a focal axis of the device. The detector may be sized and shaped to receive light collected by the plurality of lenses. The detector may be sensitive to a wavelength range propagated along the optical path. In some cases, a device may comprise an optical source, not shown. In other cases, a device may not comprise an optical source. In some cases, light propagated along a focal axis may comprise light scattered along a focal axis. In some cases, a focal axis and an ultrasound axis may also be co-linear with a pneumatic axis. A pneumatic perturbation may be propagated along a pneumatic axis.

The first and second lenses may form a first telescope. The first telescope may invert an image magnified by the first telescope. The third, fourth, and fifth lenses may comprise an erector. In some cases, a lens may be mounted on a mechanical actuator. The mechanical actuator may be configured to translate one or more lenses in order to adjust a focus of the optical assembly. For example, the mechanical actuator may comprise a motor. The motor may comprise a stepper motor. The motor may turn a screw which translates the lens. In some cases, the mechanical actuator may be controlled by a user. In some cases, the mechanical actuator is controlled automatically (e.g. by a computer program configured to find a focus). In some embodiments, fifth lens 229 may be a fine focus lens, which may be translated along axis 221.

Transducer 210 may be operably attached to mount assembly 214. Mount assembly 214 may provide an attachment mechanism for transducer 210. For example, mount assembly 214 may comprise a surface on which plate 212 is attached. For example, mount assembly 214 may center transducer 210 within a focal axis. Mount assembly may comprise a conducting portion. The conducting portion may be electrical connected to the ultrasound transducer and to a digital processing device as described herein. Mount assembly may comprise one or more apertures which may allow for the transmission of pneumatic excitation. In some cases, there may be a gap between the mount assembly and a wall of the device and/or the optical assembly, which may allow for transmission of the pneumatic excitation. In some cases, first lens 222 may be connected to mount assembly 214. In other cases, first lens 222 may not be connected to mount assembly 214.

Figure 2B:
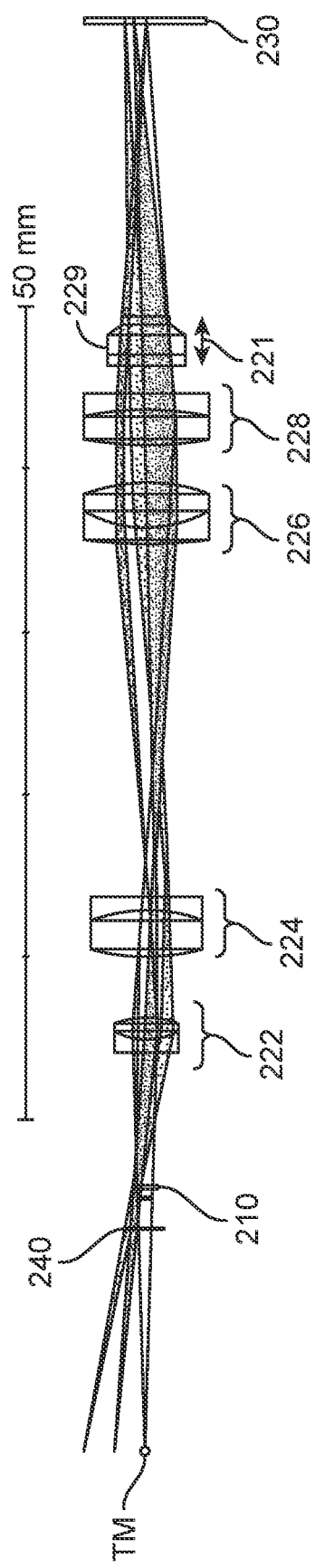
FIG. 2B illustrates a ray diagram of the device of FIG. 2A, in accordance with some embodiments.

FIG. 2B illustrates a ray diagram of the device of FIG. 2A, in accordance with some embodiments. FIG. 2B illustrates target TM and exit aperture 240. Though the optical assembly comprises a central obstruction, the optical assembly comprises a wide collection angle. As shown, first lens 222 and second lens 224 comprise a first telescope. Following the light grey line, the image collected by the first telescope inverts between second lens 224 and third lens 226. Third lens 226, fourth lens 228, and fifth lens 229 may form a second telescope. As shown, fifth lens 229 may be translated along axis 221 which may be co-linear with a focal axis of the optical assembly. Continuing to follow the light grey line, the image transmitted by the second telescope to the imaging plane may not be inverted.

Figure 3:
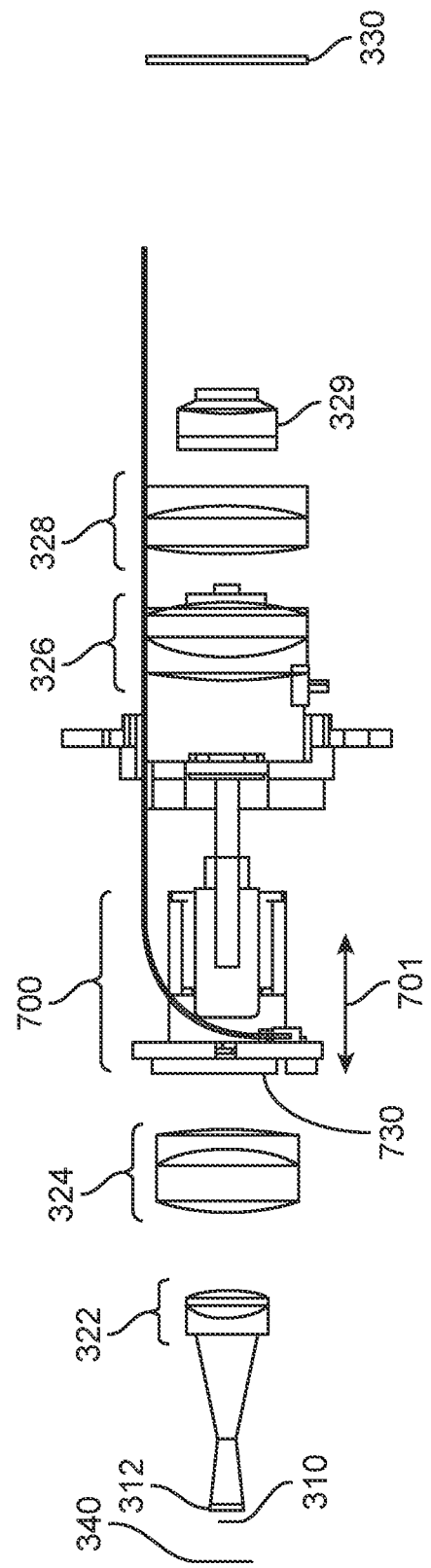
FIG. 3 is a side section view of another optical assembly for measuring optical and ultrasound signals, in accordance with some embodiments.

FIG. 3 is a side section view of another optical assembly for measuring optical and ultrasound signals, in accordance with some embodiments. FIG. 3 illustrates an example optical assembly for measuring optical and ultrasound signal with a removable camera assembly, in accordance with some embodiments. As shown, the optical assembly comprises first lens 322, second lens 324, third lens 326, fourth lens 328, and fifth lens 329. The lenses may comprise focal axes which are substantially co-axially aligned. As shown, the device comprises ultrasound transducer 310 on plate 312. Ultrasound transducer 310 may be configured to transmit ultrasound signal and/or receive ultrasound signal along an ultrasound axis. Ultrasound transducer 310 may be located on a focal axis of the optical assembly. In some cases, ultrasound transducer 310 may obstruct light propagated along a focal axis of the optical assembly. Plate 312 may be located on a focal axis of the assembly. Plate 312 may be transparent or partially transparent to light propagated along a focal axis of the device. Ultrasound transducer 310 may comprise an embodiment, variation, or example of an ultrasound transducer disclosed herein.

In some cases, a device may have an imaging plane 330. In some cases, the imaging plane may be at the surface of the detector. In some cases, the imaging plane may be at a user eye. The detector may be located along a focal axis of the device. In some cases, the device may comprise a second imaging plane. In some cases, the device may comprise a camera mount assembly 700. In some cases, the camera mount assembly may be removable. For example, the mount assembly may be removed for prototyping, assembly, and/or alignment. The camera mount assembly 700 may comprise a detector 730. The detector 730 may be moved along a focal axis 701. The detector may be moved along the image axis to improve the quality of an image, for example, by improving an image focus. In some case, the third lens 326, fourth lens 328, and fifth lens 329 may not be used. For example, an optical assembly may comprise first lens 322 and second lens 324 which may project an image on detector 730.

Detector 730 may be sized and shaped to receive light collected by the plurality of lenses. The detector may be sensitive to a wavelength range propagated along the optical path. In some cases, a device may comprise an optical source, not shown. In other cases, a device may not comprise an optical source. In some cases, light propagated along a focal axis may comprise light scattered along a focal axis. In some cases, a focal axis and an ultrasound axis may also be co-linear with a pneumatic axis. A pneumatic perturbation may be propagated along a pneumatic axis. In some cases, the optical assembly comprises exit aperture 340. The transducer 310 may obstruct the path of the optical illumination; however, light may be transmitted in an annular region around the transducer through aperture 340.

Figure 4A:
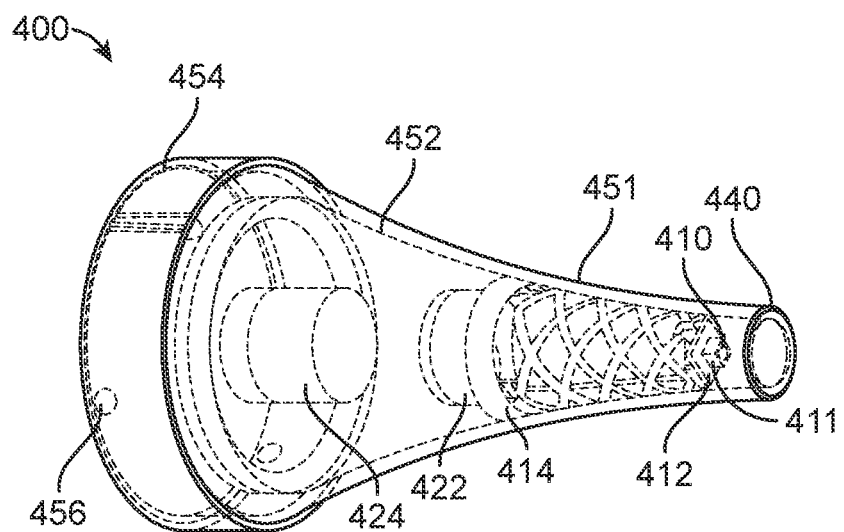
FIG. 4A is a transparent side perspective view of an example speculum comprising a light guide, in accordance with some embodiments.

FIG. 4A illustrates a transparent side perspective view of an example speculum 400 comprising a light guide, in accordance with some embodiments. A speculum of the present disclosure may comprise a transparent portion. The transparent portion may be configured to act as a light guide. For example, a speculum may comprise a transparent core 452, which may act as a light guide. A transparent portion may be configured to conduct light by total internal reflection.

As shown, the speculum may comprise a housing or shell. The housing or shell may be frustoconical in shape. The shell may comprise light transmitting core 452. In some cases, the speculum may comprise a light tight or substantially opaque shell 451. Light may be injected at the proximal portion of the frustoconical shell 454. Light may be injected at distinct insertion points around the circular proximal portion or may be injected over an extended region. In some cases, one or more fiber optics or one or more tubular light guides may be used to direct light to an insertion point.

At an insertion point, the light conducting core may meet the injected light at a steep angle. The refractive index of the transmitting core may be considered when choosing an angle of the insertion point. The angle of incidence may be chosen such that light injected will be totally internally reflected between the walls of the transparent core. The light may radially diverge within the transparent core. Accordingly, though the number of insertion points may be finite, light may emerge from the entire area of a distal tip of the speculum. The core may comprise an optical grade plastic which may be substantially free of cracks or bubbles. The core may comprise an optical material designed to support total internal reflection that is integral with the light input and light output portions. Surface treatment, e.g., polishing or reflective coating, and the continuous air gap may be used to support total internal reflection. Any suitable surface treatment, such as for example, polishing, reflective coating, anti-reflective (AR) coatings and or dielectric coatings may be used to support total internal reflection. The light conducting housing may comprise a core-cladding interface configured to limit light leaks.

Figure 16:
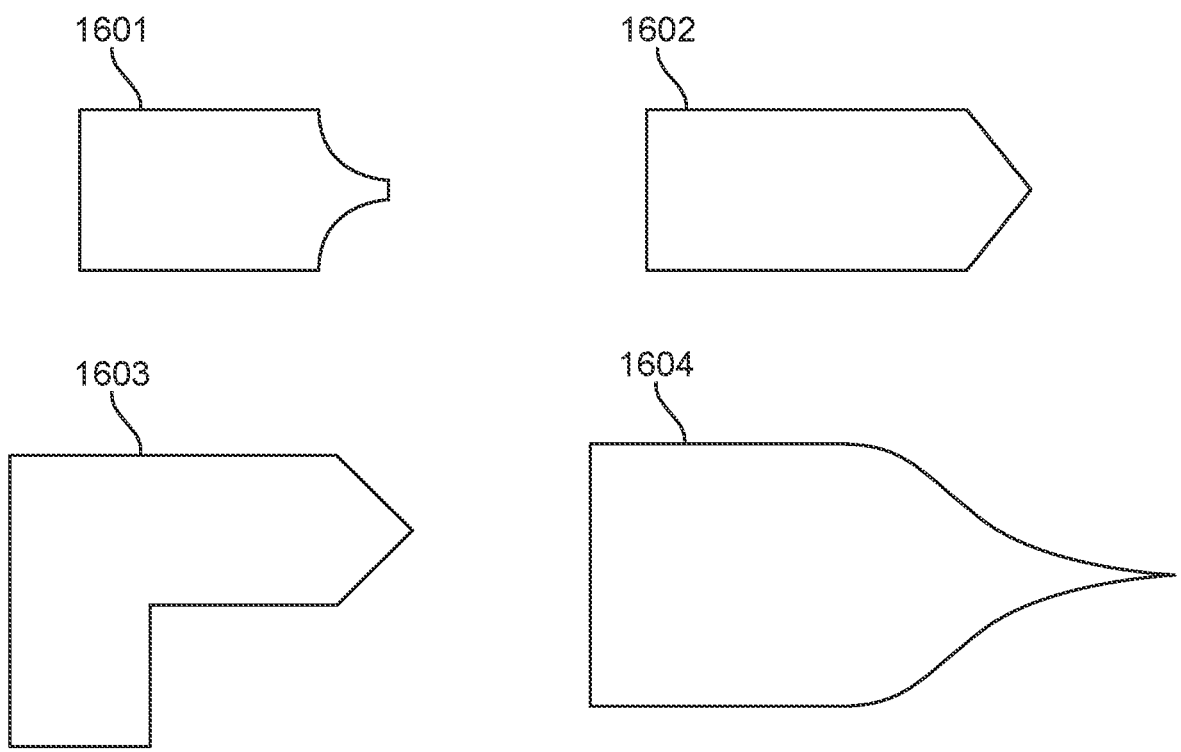
FIG. 16 illustrates example shapes of a speculum of the present disclosure, in accordance with some embodiments.

FIG. 16 illustrates example shapes of a speculum of the present disclosure, in accordance with some embodiments. A housing a speculum may comprise a shape with a tapered distal portion and a larger proximal portion. A housing of a speculum may be conical. A housing may have a distal end which is conical 1602. A housing of a speculum may comprise a tapered cone, a cone with a concave surface, or a cone with a convex surface. A housing may comprise an elbow joint in the body of the housing (e.g. 1603). A housing may taper to a fine tip (1604) or may have a truncated tip (1601).

FIG. 4A additionally illustrates example locations of an optical assembly and a central obstruction. For example, example speculum 400 may comprise a transducer mount assembly 414. Transducer mount assembly 414 may facilitate securement of transducer 410 within the speculum. Transducer mount assembly 414 may provide an attachment mechanism for transducer 410. For example, mount assembly 414 may comprise a surface on which plate 412 is attached. In some cases, plate 412 may be further connected to a transducer package base 411. An ultrasound transducer 410 may be a capacitive micromachined ultrasound transducer, which may be mounted on the package base 411. For example, mount assembly 414 may center transducer 410 within a focal axis. Mount assembly may comprise a conducting portion. The conducting portion may be electrical connected to the ultrasound transducer and to a digital processing device as described herein. Mount assembly may comprise one or more apertures which may allow for the transmission of pneumatic excitation. In some cases, there may be a gap between the mount assembly and a wall of the device and/or the optical assembly, which may allow for transmission of the pneumatic excitation. In some cases, first lens 422 may be connected to mount assembly 414. In other cases, first lens 422 may not be connected to mount assembly 414.

A speculum may comprise an inner shell on an inner side of the housing. An inner shell may comprise a shield. A shield may prevent an ultrasound signal from a transducer from being transmitted outside of the speculum. A shield may prevent electrical signal form being transmitted outside of the speculum. The shield may be a metal shield. The shield may be a conducting material. A metal shield may be disposed around the ultrasound transducer. For example, the metal shield may be radially displaced away from a transmission axis of the ultrasound transducer. The speculum may comprise a inner metallic coating or foil. The inner metallic coating or foil may be an electromagnetic shield for the transducer. In some cases, the shield may comprise a portion of an opaque shell. FIG. 4A illustrates an example placement of an optical assembly within a speculum of the present disclosure. For example, first lens 422 and second lens 424 may be aligned on co-linear focal axes. The focal axis of the optical assembly may be substantially aligned with a central axis of the speculum. The speculum may comprise exit aperture 440. In some cases, the exit aperture may be less than 10 mm in diameter. The exit aperture may be between 2 mm and 8 mm in diameter. In some cases, the transducer may be located near a distal end of the speculum. For example, the transducer may be between 1.5 cm and 1 mm from exit aperture 440.

In some cases, a speculum of the present disclosure may be disposable. A disposable speculum may facilitate cleanliness. For example, a disposable speculum may allow for the prevention of transmission of pathogenic agents from a first subject to a second subject. A device of the present disclosure may comprise a durable portion and a disposable portion. The speculum, transducer mount assembly, and transducer may comprise a disposable portion. In some cases, the optical assembly may be a portion of a durable portion. In some cases, all or part of the optical assembly may comprise a durable portion.

A speculum may have limited number of uses. For example, limited uses may be useful for hygienics, for example, for limiting spread of infection. For example, a speculum as disclosed herein may be single use. A speculum may be few uses. For example, a speculum may be used less than 20 times, less than 10 times, less than 5 times, or less. A speculum may be used multiple times for a single subject or a single bodily lumen of a subject. For example, a speculum may comprise a fitting which deforms or otherwise changes in shape to limit to a single use. A speculum may comprise a physical and/or electronic label which may be registered by a digital processing device and validated for a single use. The components of a speculum disclosed herein may be sufficiently inexpensive to allow for disposal of the speculum after a single or few uses.

The speculum may comprise an interface for connecting to a durable portion. The interface may be light sealed. The interface may be air sealed. An air seal may aid in the transmission of a pneumatic excitation from a pressure source to a target along a pneumatic axis. The interface may comprise one or more alignment guides. An alignment guide may comprise a raised portion or a lowered portion which may serve to radially align the speculum with a durable portion. An axial alignment may aid in forming an electrical connection and/or an optical connection. An alignment guide may comprise a raised portion or a lowered portion which may serve to axially align a speculum with a durable portion. Example 400 comprises an axially alignment guide 456 and a radially alignment guide.

Figure 4B:
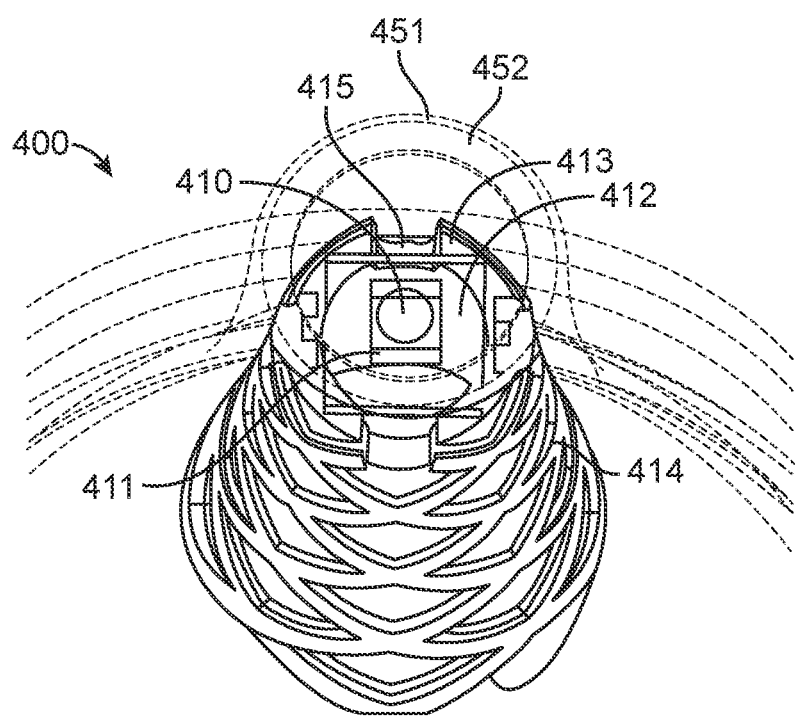
FIG. 4B is a transparent isomorphic view of the speculum of FIG. 4A, in accordance with some embodiments.

FIG. 4B illustrates a transparent isomorphic view of example speculum 400 comprising a light guide, in accordance with some embodiments. FIG. 4B illustrates a detail view of the distal tip of an example speculum 400. The distal tip may comprise ultrasound transducer 410 on transducer package base 411. The package base may be mounted on plate 412. Plate 412 may comprise an optically transparent portion. The distal end of the transducer mount assembly 414 may comprise one or more electrical contact pads 413. The electrical contact pads may be electrically connected to electrical contact on the surface of the transducer 410. The plate 412 may be substantially insulating. The electrical contact pads may be connected to a conducting portion of the transducer mount assembly which may be releasably electrically connected to a digital processing device as described elsewhere herein.

FIG. 4B illustrates a distal tip of the speculum. The distal tip may comprise a transparent core 452 and an opaque shell 451. The housing of the speculum may transmit light from a proximal portion of the speculum to a distal tip of the speculum. Light may be propagated to a target. Light may be reflected from a target through exit aperture 440 into a central lumen of the speculum. Light may be received from a target though exit aperture 440 around the transducer 410 and through a transparent portion of plate 412. Pneumatic excitation may be transmitted from the lumen of the speculum through one or more pneumatic apertures 415. The pneumatic excitation may be sufficiently small as to not cause detachment of plate 412.

A speculum of the present disclosure may comprise an outer surface 451. The outer surface in some cases may be opaque. The outer surface may be coated to provide a seal against a wall of a lumen to be measured. For example, the outer surface may comprise a soft coating or membrane which may provide an improved air seal against a biological lumen (e.g. an ear canal).

Figure 5A:
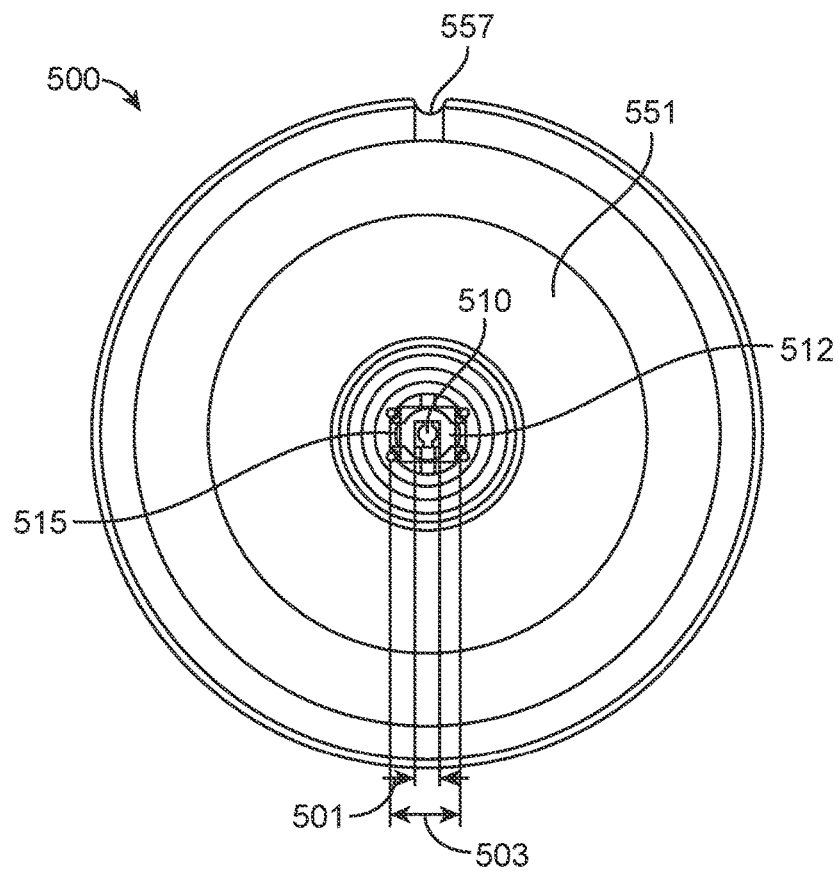
FIG. 5A is a front view of the distal tip of an example speculum comprising one or a plurality of optic fibers, in accordance with some embodiments.
Figure 5B:
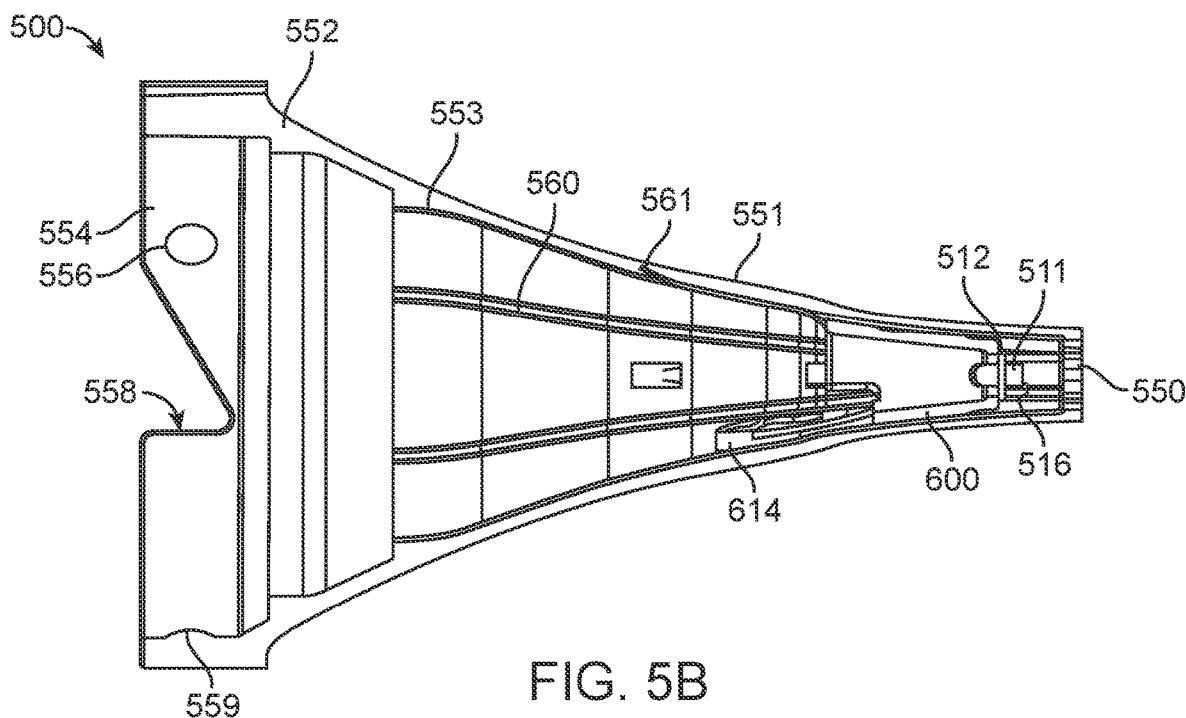
FIG. 5B is a transparent side view of the speculum of FIG. 5A, in accordance with some embodiments.

FIG. 5B illustrates a transparent side view of example speculum 500 comprising one or a plurality of optic fibers, in accordance with some embodiments. A speculum of the present disclosure may comprise one or more optic fibers. For example, in the illustrated embodiment, a speculum may comprise one or more optic fibers 560. In the illustrated example, the speculum may comprise 4 optic fibers; however, the speculum may comprise a number of optic fibers within a range from 1 to 1000, 1 to 100, or 1 to 10. The one or more optic fibers may be configured to conduct light by total internal reflection.

As shown, the speculum 500 may comprise a housing or shell. The housing or shell may be frustoconical in shape. The housing or shell may comprise body portion 552. The housing may comprise outer shell 551 exterior to body portion 552. The housing may comprise inner housing 553. Inner housing 553 and body portion 552 may secure one or more optic fibers 560 within the housing. In some cases, the body portion may be transparent as disclosed elsewhere herein. In some cases, the body portion may be opaque. The body portion may be a plastic or a glass.

Inner housing 553 may comprise attachment members 561. In some cases, inner housing 553 may be removable from body portion 552. Inner housing 553 and body portion 552 may be glued, may be press fit, may be welded, etc. Inner housing 553 may be comprise attachment members which may snap inner housing 553 in to place or may friction fit inner housing 553 in to place. In some cases, inner housing 553 may aid in securing transducer mount assembly 600.

Inner housing 553 may comprise an electromagnetic shield. A shield may prevent an ultrasound signal from a transducer from being transmitted outside of the speculum. A shield may prevent electrical signal form being transmitted outside of the speculum. The shield may be a metal shield. The shield may be a conducting material. A metal shield may be disposed around the ultrasound transducer. For example, the metal shield may be radially displaced away from a transmission axis of the ultrasound transducer. The speculum may comprise a inner metallic coating or foil. The inner metallic coating or foil may be an electromagnetic shield for the transducer. In some cases, the shield may comprise a portion of an opaque shell 551.

A speculum of the present disclosure may comprise an outer surface 551. The outer surface in some cases may be opaque. The outer surface may be coated to provide a seal against a wall of a lumen to be measured. For example, the outer surface may comprise a soft coating or membrane which may provide an improved air seal against a biological lumen (e.g. an ear canal).

In some cases, the speculum may comprise a light tight or substantially opaque outer shell. Light may be injected at the proximal portion of the one or more optic fibers near a proximal end of the frustoconical portion. Light may be injected at all or a subset of the one or more optic fibers. In some cases, one or more fiber optics or one or more tubular light guides may be used to direct light from a body of the device to an insertion point near the proximal end of the frustoconical portion.

FIG. 5B additionally illustrates transducer mount assembly 600. Transducer mount assembly 600 may facilitate securement of transducer 510 within the speculum. Transducer mount assembly 600 may provide an attachment mechanism for transducer 510. For example, mount assembly 600 may comprise a surface on which plate 512 is attached. In some cases, plate 512 may be further connected to a transducer package base 511. An ultrasound transducer 510 may be a capacitive micromachined ultrasound transducer, which may be mounted on the package base 511. For example, mount assembly 600 may center transducer 510 within a focal axis. Mount assembly 600 may comprise a conducting portion 614. The conducting portion may be electrically connected to the ultrasound transducer and to a digital processing device as described herein. An electrical connection may comprise one or more wires 516. Mount assembly 600 may comprise one or more apertures 515 which may allow for the transmission of pneumatic excitation. In some cases, there may be a gap between the mount assembly and a wall of the device and/or the optical assembly, which may allow for transmission of the pneumatic excitation.

The speculum may comprise exit aperture 540. In some cases, the exit aperture may be less than 10 mm in diameter. The exit aperture may be between 2 mm and 8 mm in diameter. In some cases, the transducer may be located near a distal end of the speculum. For example, the transducer may be between 1.5 cm and 1 mm from exit aperture 540. The speculum may comprise an outer diameter sized and shaped to fit within an external ear canal of a patient.

Speculum 500 may comprise an interface 554 for connecting to a durable portion. The interface may be light sealed. The interface may be air sealed. An air seal may aid in the transmission of a pneumatic excitation from a pressure source to a target along a pneumatic axis. The interface may comprise one or more alignment guides (e.g. 556, 557, 558, 559). An alignment guide may aid in forming an electrical connection and/or an optical connection. A radial alignment guide may comprise a raised portion or a lowered portion which may serve to radially align the speculum with a durable portion. For example, radial alignment guide 557 may provide an external indication of a radial alignment of a speculum. For example, radial alignment guide 556 may provide an internal, releasable stop to a rotation. Radial alignment guide 558 may aid in quick release of the speculum. A quick release may be engaged and/or disengaged by an external mechanism such as a twisting mechanism or a pulling mechanism. An axial alignment guide may comprise a raised portion or a lowered portion which may serve to axially align a speculum with a durable portion. For example, axial alignment guide 559 may fit into a groove on a durable portion to aid in a tactile sense of a seal. For example, alignment guide 556 may also serve as an axial alignment guide.

FIG. 5A illustrates a detail view of the distal tip of an example of a speculum 500, in accordance with some embodiments. The distal tip may comprise ultrasound transducer 510 on transducer package base 511. The package base may be mounted on plate 512. Plate 512 may comprise an optically transparent portion. The one or more optic fibers with the speculum may transmit light from a proximal portion of the speculum to a distal tip of the speculum. Light may be propagated to a target. Light may be reflected from a target through exit aperture 540 into a central lumen of the speculum. Light may be received from a target though exit aperture 540 around the transducer 510 and through a transparent portion of plate 512. Pneumatic excitation may be transmitted from the lumen of the speculum through one or more pneumatic apertures 515. The pneumatic excitation may be sufficiently small as to not cause detachment of plate 512.

FIG. 5A also illustrates dimensions 501 and 503. Dimension 501 may comprise a distance spanned by the central obstruction measured normal to the optical axis. A central obstruction may be a transducer package base. In some embodiments, the substrate is disposed on a carriage material, which may be a part of a base. The base may allow for mounting of the ultrasound transducer on a device of the present disclosure. For example, the base may be mounted on a tip of speculum described elsewhere herein. The base may comprise electrical connections such as wiring, vias, etc. to conduct electrical signals from the ultrasound transducer to a digital processing device. The base may protect the ultrasound transducer. The base may stiffen and/or provide additional support to the substrate of the ultrasound transducer. The base may comprise a portion of the wafer upon which an ultrasound transducer was manufactured. The package base may be a square with dimension of 0.1 to 3 mm per side. The package base may be a rectangle with sides of 0.1 to 4 mm and 0.1 to 4 mm. The package base may be a circle with a diameter of 0.1 to 3 mm.

Dimension 503 may comprise a largest dimension of aperture 550. Aperture 550 may comprise a circular shape, an ellipsoid shape, a regular polygonal shape, an irregular shape, etc. Aperture 550 may comprise a largest distance measured along an axis normal to the focal axis of 0.2 to 10 mm, 1 mm to 8 mm, or 2 mm to 5 mm. Dimension 503 may be less than 5 mm. Dimension 503 may be sized and shaped to fit within an ear of a subject.

Dimension 501 may be less than dimension 503. A central obstruction may subtend a solid angle within the aperture 550 which is less than 90% of the solid angle subtended by aperture 550 as measured from the most distal lens of the optical assembly. In some cases, dimension 501 is roughly 75% of dimension 503. In some cases, dimension 501 is roughly half of dimension 503. In some cases, dimension 501 is between 20% and 80% of dimension 503. In some cases, an exit aperture has about a 70% clear area and about a 30% obstructed area. In some cases, an exit aperture has less than about a 75% obstructed area. In some cases, the transducer may be set back about 2 mm or less from an exit aperture. An obstructed area at the exit aperture may comprise a projection of the obstructed area onto the plane of the aperture.

Figure 6A:
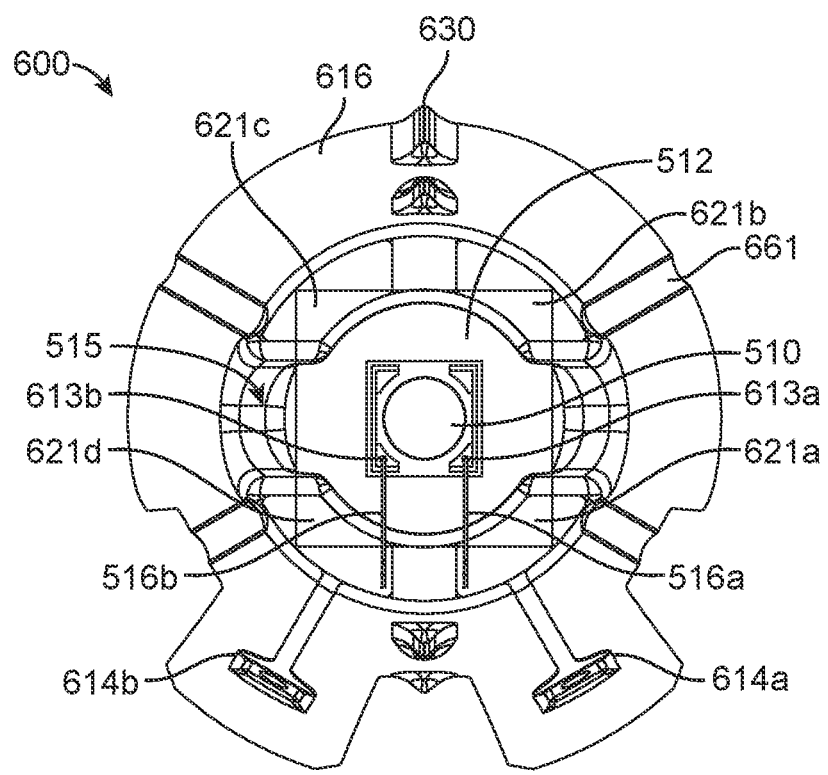
FIG. 6A is a front view of a distal end of a transducer mount assembly, in accordance with some embodiments.
Figure 6B:
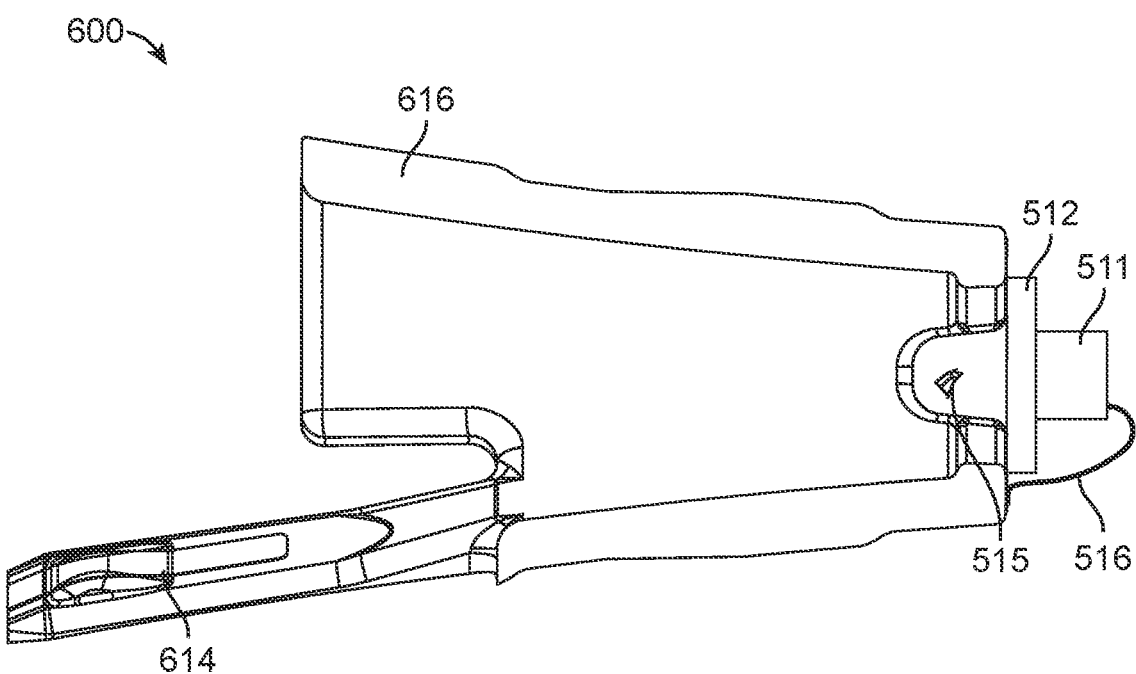
FIG. 6B is a side cross section view of the transducer mount assembly of FIG. 6A, in accordance with some embodiments.

FIG. 6B illustrates a side cross section view of transducer mount assembly 600, in accordance with some embodiments. Transducer mount assembly 600 may provide an attachment mechanism for transducer 510. Mount assembly 600 may comprise body portion 616. Mount assembly 600 may comprise a surface on which plate 512 is attached and which may comprise a portion of body 616. In some cases, plate 512 may be further connected to a transducer package base 511. An ultrasound transducer 510 may be a capacitive micromachined ultrasound transducer, which may be mounted on the package base 511. In the illustrated example, mount assembly 600 may center transducer 510 within a focal axis. Mount assembly 600 may comprise one or more apertures 515 which may allow for the transmission of pneumatic excitation. In some cases, there may be a gap between the mount assembly and a wall of the device and/or the optical assembly, which may allow for transmission of the pneumatic excitation. The conducting portion may be electrically connected to the ultrasound transducer and to a digital processing device as described herein. An electrical connection may comprise one or more wires 516.

FIG. 6A illustrates a front view of a distal end of transducer mount assembly 600, in accordance with some embodiments. In the illustrated embodiment, transducer mount assembly 600 may comprise body portion 616. Body portion 616 may comprise securement device 630 on an exterior surface thereof. One or more securement device may maintain a transducer mount assembly in place within a speculum. Body portion 616 may comprise one or more grooves 661. For example, a distal portion of one or more optic fibers may be disposed within grooves 661. The light may be transmitted from a distal end of one or more optic fibers near a distal end of the transducer mount assembly. Body portion 616 may comprise an electrically conducting portion. Assembly 600 illustrates an extended tail with an electrical interface 614. Interface 614 may form an electrical contact with a durable portion of a device as disclosed herein. Interface 614 may comprise contacts 614*a* and 614*b*.

FIG. 6A also illustrates a view of ultrasound transducer 510 on a transducer package base 511. Transducer 510 may comprise a plurality of ultrasound transducer elements arranged in a circle on package base 511. The package base may comprise one or more electrical contact pads (e.g. 613*a*, 613*b*, 613*c*, 613*d*). The electrical contact pads may be connected by conductors (e.g. 516*a* and 516*b*) to one or more electrical contact pads of the transducer mount assembly. Transducer mount assembly 600 may comprise one or more electrical contact pads (e.g. 621*a*, 621*b*, 621*c*, 621*d*). The electrical contact pads may be electrically connected to electrical contact on the surface of the transducer 610. The plate 512 may be substantially insulating. The electrical contact pads may be connected to a conducting portion of the transducer mount assembly which may be releasably electrically connected to a digital processing device as described elsewhere herein. Plate 512 may incompletely cover a distal end of a transducer mount assembly. As shown, the transducer mount assembly may comprise pneumatic apertures 515, which may allow for a gas such as air to pass around an ultrasound transducer.

FIG. 7A illustrates a side cross section view of detector assembly 700, in accordance with some embodiments. FIG. 7B illustrates a side view of the detector assembly of FIG. 7A, in accordance with some embodiments. Detector assembly 700 may comprise detector 730. Detector 730 may be aligned to receive an image from an optical assembly of the present disclosure. Detector 730 may be translated along axis 701. Axis 701 may be parallel and/or co-axial with a focal axis of the optical assembly. Detector 730 may be mounted on detector plate 732. Detector plate 732 may provide a mechanical and electrical interface between a detector and a digital processing device as described elsewhere herein. A conductor 734 may conduct electrical signals between detector 730 and a digital processing device.

Detector 730 may be mechanically translated. In some cases, detector 730 may be mounted on a mechanical actuator. The mechanical actuator may be configured to translate detector 730 in order to adjust a focus of the optical assembly. For example, the mechanical actuator may comprise a motor 752. The motor may comprise a stepper motor. The motor may turn screw 742 which translates the detector. In some cases, the mechanical actuator may be controlled by a user. In some cases, the mechanical actuator is controlled automatically (e.g. by a computer program configured to find a focus). A translatable detector may be used with an optical assembly with fixed lenses; however, a translatable detector may also be used in a system with movable lenses. An image from a detector 730 may be processed, modified, or corrected by a digital processing device.

In some cases, detector 730 may not be removable from the device. In embodiments which do not have detector, a user eye may not be perfectly aligned with a transmission axis of the ultrasound energy. This may not be ideal in cases where a user manually aligns a device with a target. If a user eye is not aligned with a transmission axis of the ultrasound, the ultrasound may be incorrectly pointed. A detector mounted within the device center a focal axis along an ultrasound transmission axis. A detector mounted within the device may improve alignment of ultrasound and optical excitation on a target. For example, a detector mounted and centered on a focal axis of the optical assembly may be used as a reference and/or may be a sufficient reference for an axis of propagation of the ultrasound excitation. The ultrasound, which may be co-axial with the focal axis, may be aimed by putting the target at the center of the detected optical image. An optical image may be used as a surrogate for the ultrasound propagation. The optical image may be used in addition to aligning for an amplitude of the reflected ultrasound signal. An alignment aid on a display visible to a user may further aid in alignment of the ultrasound excitation. As ultrasound excitation is not visible to a user, improved alignment may be important. Detector 730 may be removably coupled to the devices as disclosed herein using attachment 754. In some cases, a detector may be removed for prototyping, alignment, etc., and a detector may be replaced for long term use.

Figure 8B:
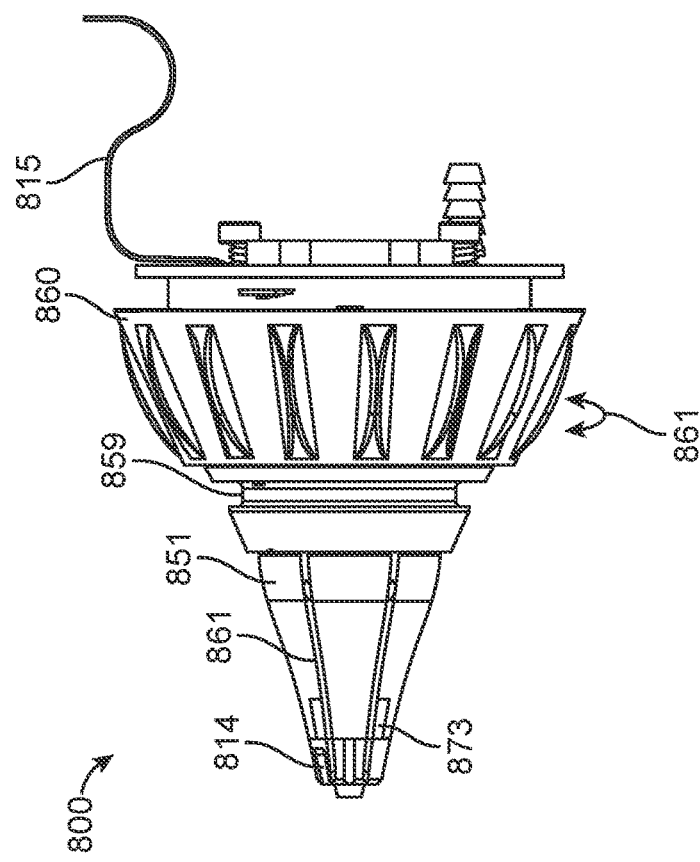
FIG. 8B is a side view of the interface of FIG. 8A, in accordance with some embodiments.
Figure 8A:
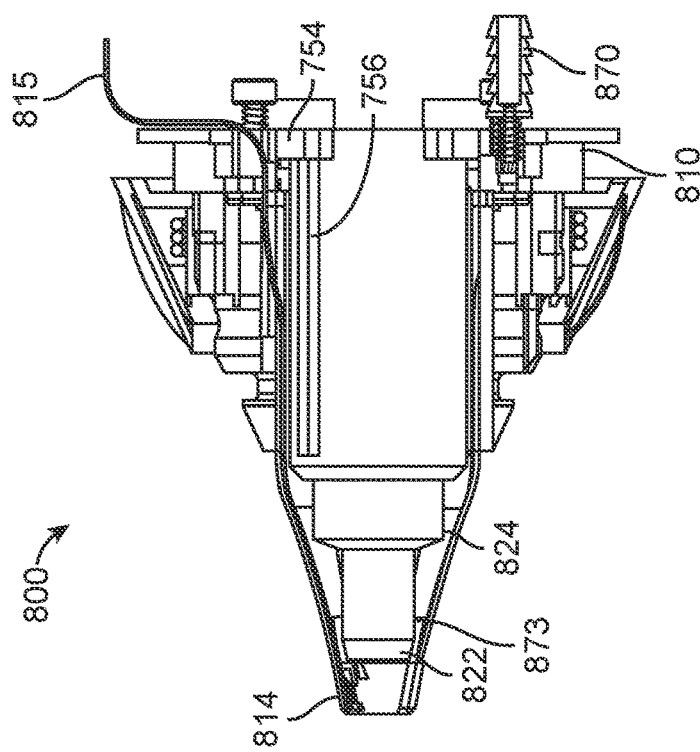
FIG. 8A is a side section view of an example interface for receiving a speculum, in accordance with some embodiments.

FIG. 8A illustrates a side section view of interface 800 for receiving a speculum, in accordance with some embodiments. FIG. 8B illustrates a side view of the interface of FIG. 8A for receiving a speculum, in accordance with some embodiments. Interface 800 may comprise a tapered distal end sized and shaped to receive a speculum of the present disclosure. Interface 800 may comprise a proximal end 810 which may interface with a body of a device, not shown. Interface 800 comprises surface 851 which may interface with a speculum of the present disclosure. In some cases, a gap to facilitate transmission of a pneumatic excitation may be present between a surface of the interface and a surface of the speculum.

Interface 800 may facilitate removable coupling of a speculum. Interface 800 comprises actuator 860. Actuator 860 may be rotated along axis 861 in order to lock and/or release a speculum. Interface 800 may comprise one or more alignment guides (e.g. 859, 861) which may facilitate attachment of a speculum. For example, groove 859 may interface with alignment guide 559 of speculum 500 to axially align a speculum. For example, grooves 861 may interface with raised portions of a speculum corresponding to one or more optic fibers. Grooves 861 may provide rotational alignment of a speculum.

Interface 800 may allow for transmission of a pneumatic excitation from a body of the device to a distal end of the speculum. Interface 800 illustrates tube fitting 870 which may be connected to a pressure source within a body of the device. In some cases, pneumatic excitation is transmitted from fitting 870 into an interior of the interface and out through a distal tip of the interface. In some cases, pneumatic excitation is transmitted partially though the housing 810, though a channel behind groove 859, along an inside surface of the speculum and through aperture 873 toward a distal tip of the speculum.

Interface 800 may allow for transmission of electrical signal to and from a body of the device and a speculum. In the illustrated embodiment, a distal tip of interface 800 comprises conducting a nose cone with electrical connect 814. For example, electrical connect 814 may receive electrical interface 614 of transducer mount assembly 600. Electrical connect 814 may be connected by wire 815 to a digital processing device.

Interface 800 may provide mechanical support for one or more mirrors of an optical assembly as disclosed herein. In the illustrated embodiment, an interior of interface 800 comprises socket 822 and socket 824. The sockets 822 and 824 may receive first and second lenses of an optical assembly. FIG. 8A also illustrates display attachment 754 which may allow connection of a detector assembly 700 to interface 800. Also shown is guide post 756 which may aid in stabilization of translation of detector 730.

Figure 9:
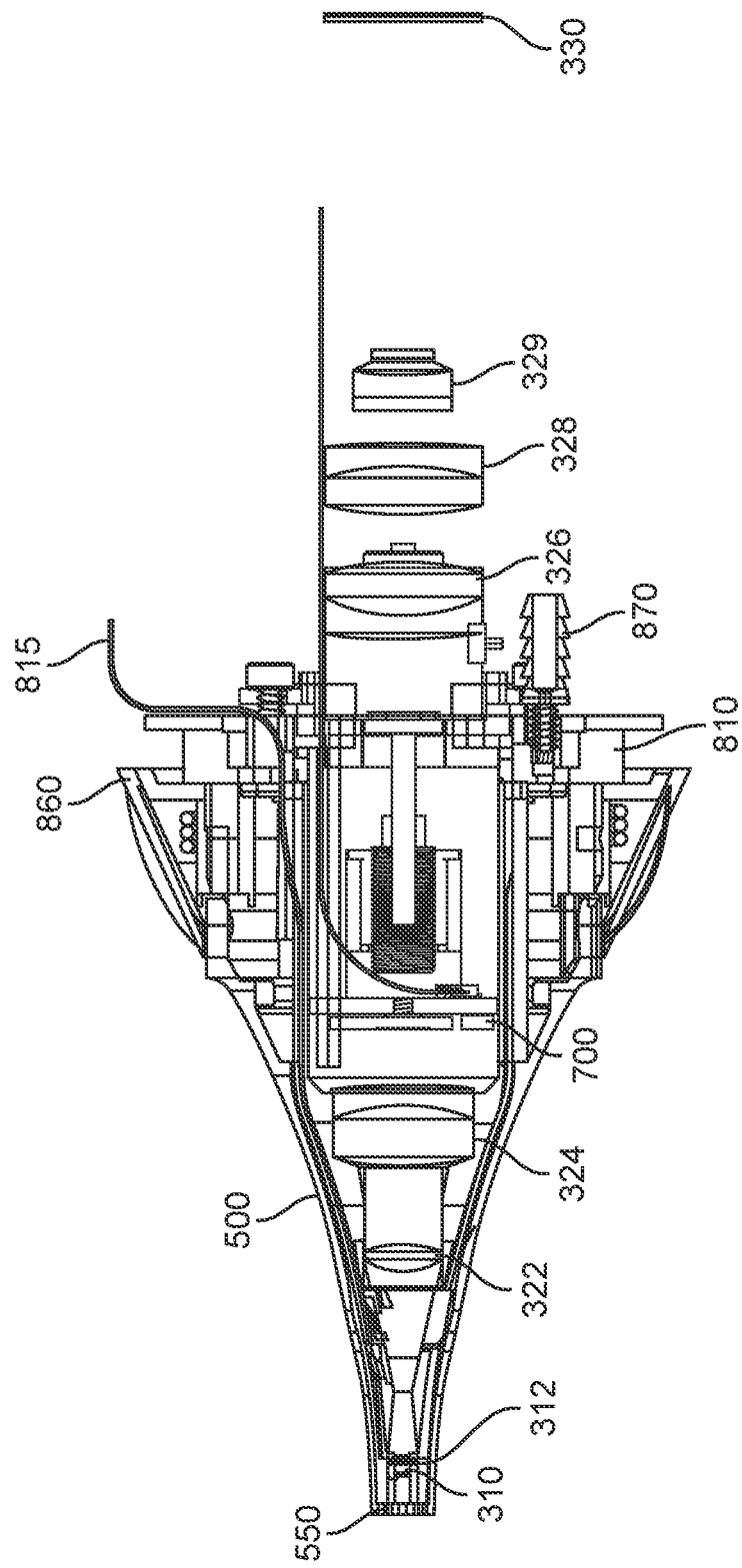
FIG. 9 is a side section view of an example speculum connected to an interface, in accordance with some embodiments.

FIG. 9 is a side section view of an example speculum connected to an interface, in accordance with some embodiments. FIG. 9 illustrates speculum 500 connected to interface 800, in accordance with some embodiments. Speculum 500 may be releasably connected to interface 800. A lock and/or release of speculum 500 may be actuated by actuator 860. Interface 800 may be mechanically connected to a body of the device at proximal portion 810. Interface 800 may be electrically connected to a body of the device at 815. Interface 800 may be pneumatically connected to a body of the device at 870. Light, ultrasound, and gas may be transmitted from a body of the device through a distal tip 550 to a target. Light, ultrasound, and gas may be received from a target through a distal tip 550 to a body of the device.

FIG. 9 illustrates an example placement of an optical assembly within an interface of the present disclosure. For example, first lens 322 and second lens 324 may be aligned on co-linear focal axes. The focal axis of the optical assembly may be substantially aligned with a central axis of the speculum. FIG. 9 illustrates optional lenses 326, 328, and 329 as well as image plane 330. As shown, the speculum comprises ultrasound transducer 310 on plate 312. Ultrasound transducer 310 may be configured to transmit ultrasound signal and/or receive ultrasound signal along an ultrasound axis. Ultrasound transducer 310 may be located on a focal axis of the optical assembly. In some cases, ultrasound transducer 310 may obstruct light propagated along a focal axis of the optical assembly. Plate 312 may be located on a focal axis of the assembly. Plate 312 may be transparent or partially transparent to light propagated along a focal axis of the device. Ultrasound transducer 310 may comprise an embodiment, variation, or example of an ultrasound transducer disclosed herein.

Figure 11:
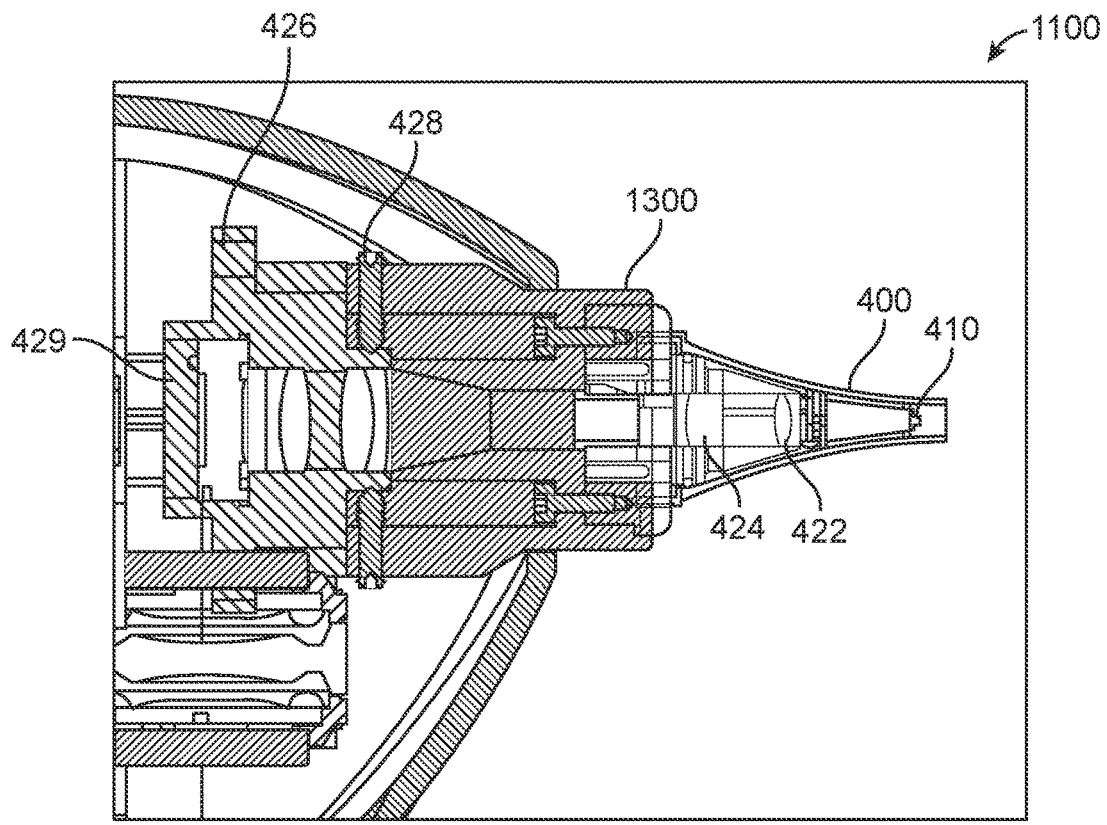
FIG. 11 is a side view of an example device comprising an interface for receiving speculum comprising a light guide, in accordance with some embodiments.
Figure 13:
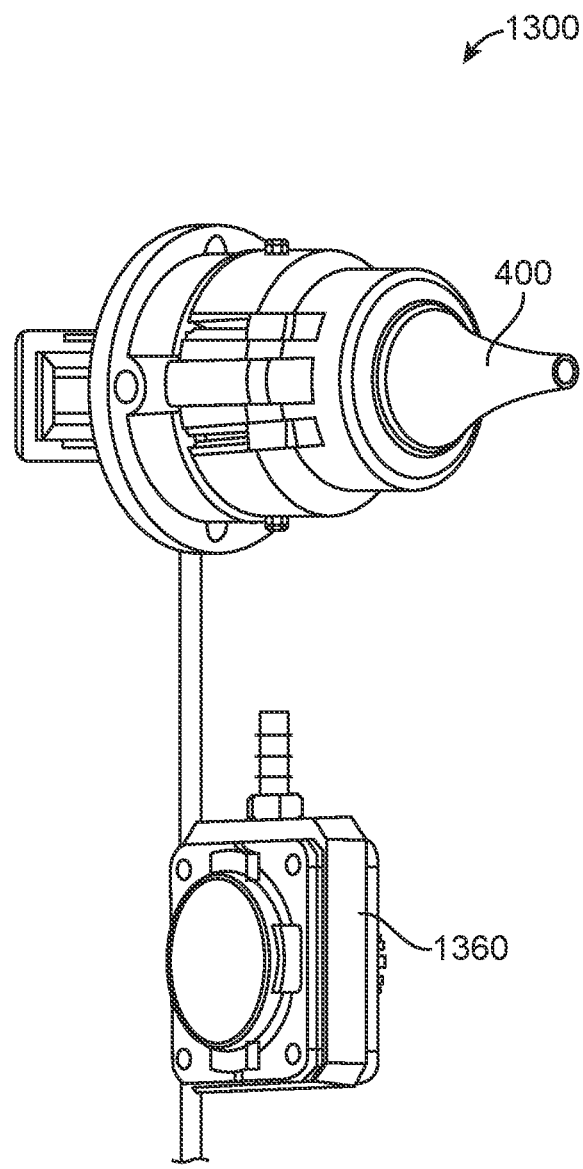
FIG. 13 is a perspective view of an example interface connected to a pneumatic subsystem, in accordance with some embodiments.

FIG. 11 is a side view of an example device 1100 comprising interface 1300 for receiving speculum 400, in accordance with some embodiments. Speculum 400 may comprise a transparent core, which may act as a light guide. A transparent portion may be configured to conduct light by total internal reflection. Light may be injected at the proximal portion of the frustoconical shell. As shown, the optical assembly comprises first lens 422, second lens 424, third lens 426, fourth lens 428, and fifth lens 429. The lenses may comprise focal axes which are substantially co-axially aligned. As shown, the device comprises ultrasound transducer 410. FIG. 13 illustrates interface 1300 connected to a pneumatic subsystem 1360, in accordance with some embodiments. Pneumatic subsystem 1360 may be within a body portion of a device. In some examples, interface 1300 may connect to speculum 400.

Figure 12:
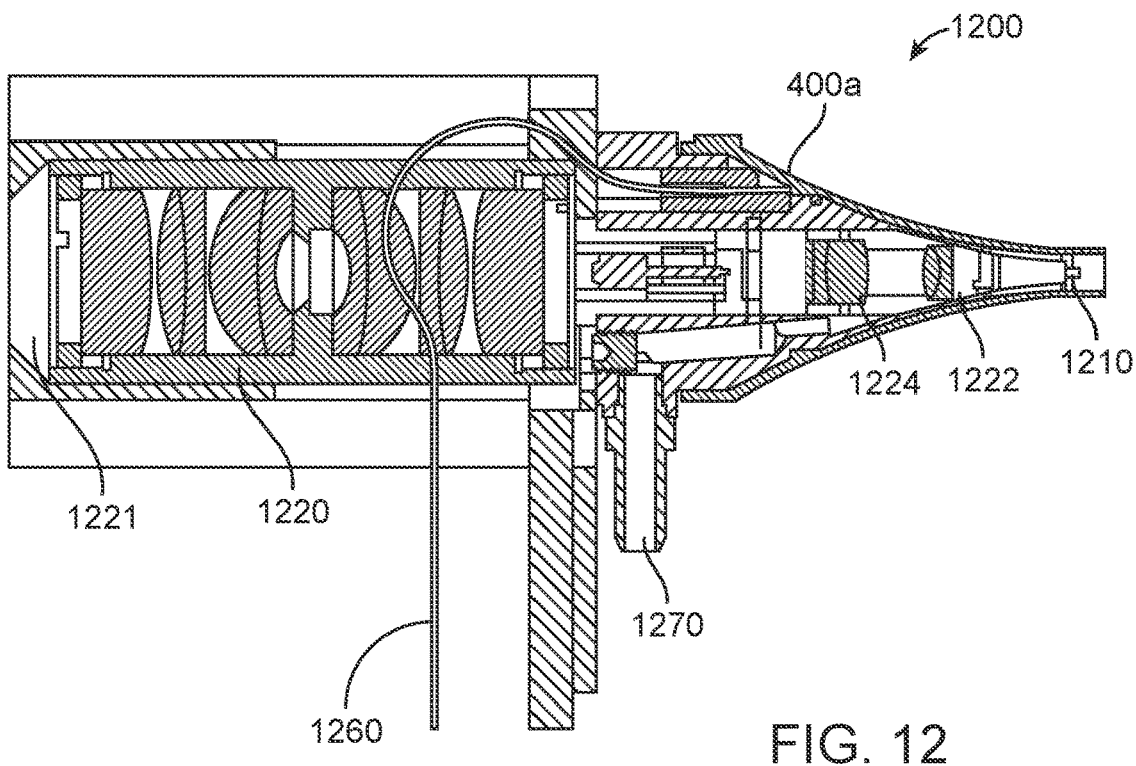
FIG. 12 is a side view of an example device connected to a speculum comprising a light guide and a light insertion point, in accordance with some embodiments.

FIG. 12 is a side view of an example device 1200 connected to a speculum comprising a light guide and a light insertion point, in accordance with some embodiments. As shown, speculum 400*a* may comprise a transparent core, which may act as a light guide. A transparent portion may be configured to conduct light by total internal reflection. Light may be injected at an injection point on an interior of the frustoconical shell. An optic fiber 1260 may connect a light source within an interior of the device to an insertion point. As shown, the device comprises ultrasound transducer 1210. As shown, the optical assembly comprises first lens 1222, second lens 1224, and relay lens assembly 1220. The lenses may comprise focal axes which are substantially co-axially aligned. The relay lens assembly may invert an image from first lens 1222 and second lens 1224. The relay lens may comprise a viewing port 1221, which may allow a user to view an image transmitted by the optical assembly. FIG. 12 also illustrates a port 1270 which may allow a pressure excitation to be conducted to a distal tip of a speculum 400*a*.

Figure 10A:
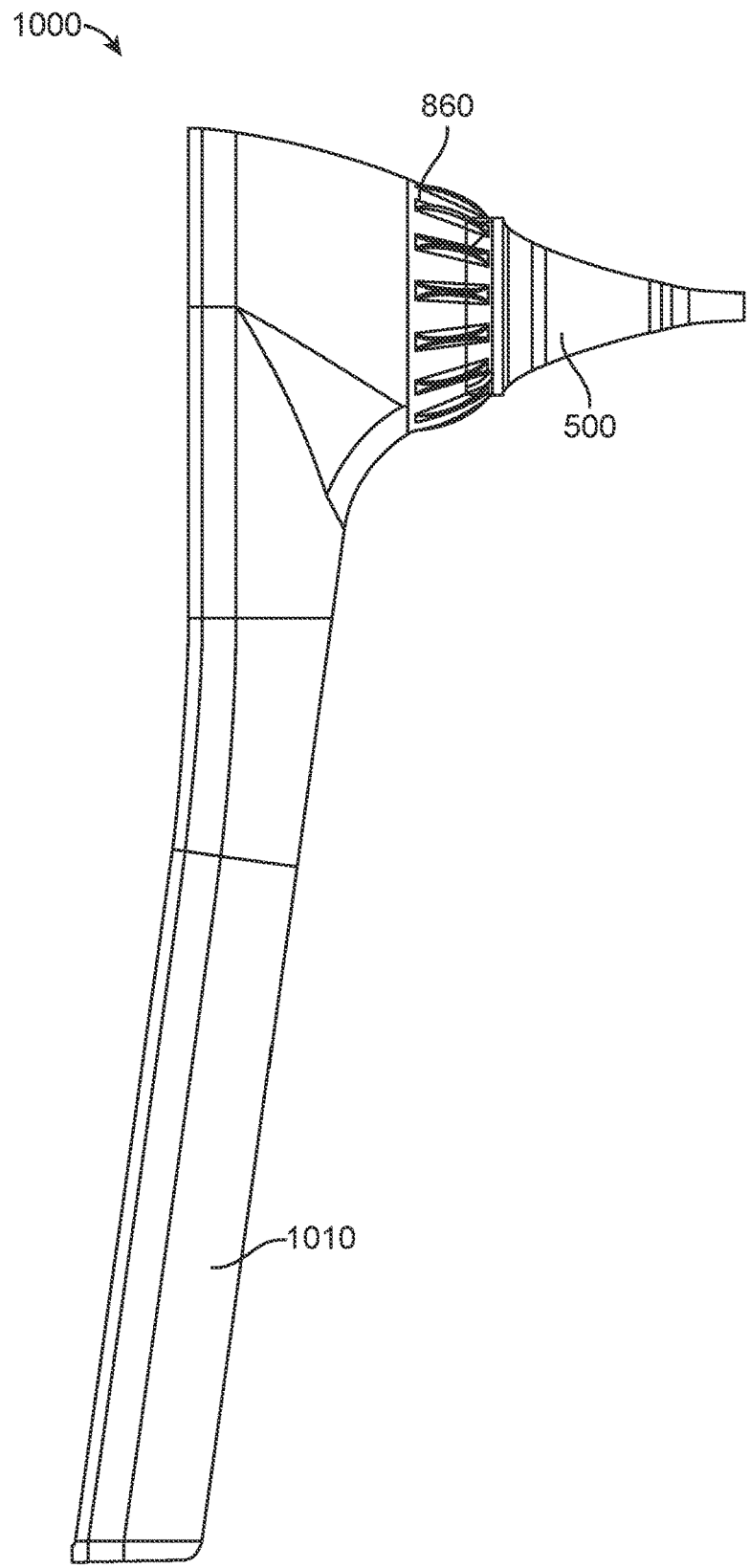
FIG. 10A is a side view of an example device body coupled to an interface and a speculum, in accordance with some embodiments.

FIG. 10A illustrates a side view of an example of device body coupled to an interface and a speculum, in accordance with some embodiments. Device 1000 may comprise handle portion 1010. Device 1000 may comprise and/or be attached to interface 800. Speculum 500 may be connected to interface 800. Actuator 860 may lock and/or release speculum 500. Device 1000 may comprise control mechanisms, which may include a digital processing device, within a handle portion 1010. Control mechanisms for the various components of the device are described in further detail with reference to FIG. 10B.

Figure 10B:
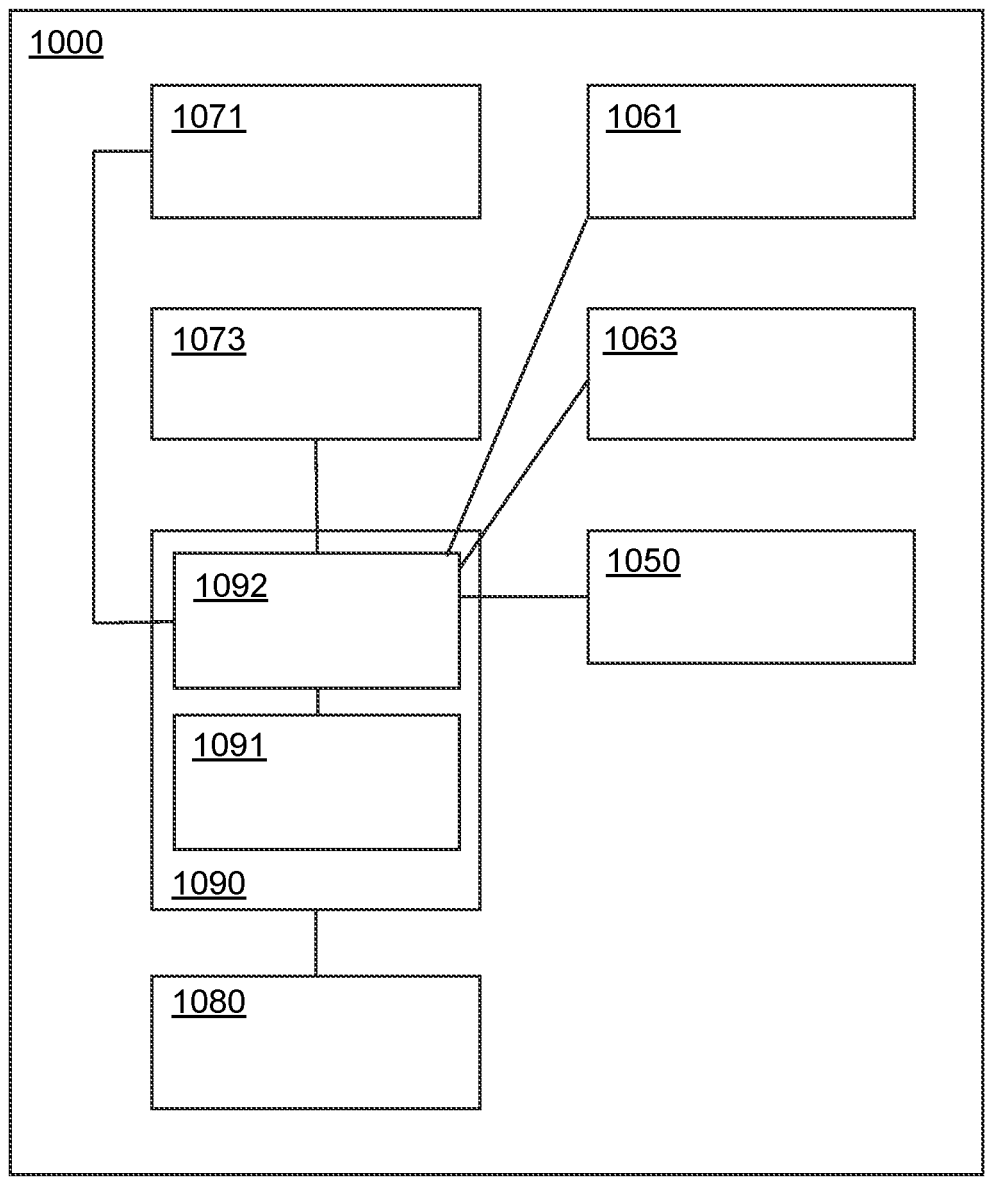
FIG. 10B is a schematic diagram of the device FIG. 10A, in accordance with some embodiments.

FIG. 10B illustrates a schematic of a device body 1000, in accordance with some embodiments. Device 1000 may comprise pneumatic driver 1071 within the body of the device. In some examples, a pneumatic driver may be an excitation generator. The excitation generator may be an air bladder manipulated by an operator to apply a force to a membrane or surface, an air displacement generator producing alternating pressure, step pressure, or air puffs. The excitation generator output may be a puff of gas such as atmospheric air or other suitable gas. In some examples, an excitation generator or a pneumatic driver is a voice coil actuator. In some examples, the excitation generator may produce a sonic excitation, a sub-sonic excitation, or a super-sonic excitation. For example, the excitation generator may produce a sub-audio frequency below 20 Hertz (Hz), an audio frequency from 20 Hz to 20 kilohertz (kHz), or a super-audio frequency above 20 kHz. In an example, a sonic excitation, a sub-sonic excitation, or a super-sonic excitation may be produced by a piezoelectric transducer. The piezoelectric transducer may convert an electrical signal to a physical displacement which may in turn induce a pressure wave. In an example, a sonic excitation, a sub-sonic excitation, or a super-sonic excitation may be produced by a capacitive micromachined ultrasound transducer.

Device 1000 may comprise pressure sensor 1073. A pressure sensor may be used to track a frequency and/or intensity of a pneumatic excitation. A pressure sensor may be used to determine if a pneumatic excitation has occurred. A pressure sensor may be used to determine if a pressure within a bodily lumen has become too high and/or prevent a pressure within a bodily lumen becoming too high. A pressure that is too high may be a pressure that is unsafe for a subject. Pressure sensor may comprise a quality control parameter. For example, in cases where a pressure increase around a pneumatic excitation is lower than a threshold, a digital processing device may alert a user to retake the measurement.

Device 1000 may comprise an optical source 1061. An optical source may comprise an LED. An optical source may comprise a laser. An optical source may comprise a light bulb. An optical source may comprise an optic fiber which terminates outside of the housing and collects ambient light. Device 1000 may comprise driving circuitry for the optical assembly 1063. Driving circuitry for the optical assembly may comprise motor controls for a movable lens and/or a display assembly. Driving circuitry for the optical assembly may comprise display control circuitry.

Device 1000 may comprise transducer drive circuitry 1050. In some cases, a transducer drive circuitry may be integrated with an on-board digital processing device 1090 or microprocessor 1091 as described herein. Transducer drive circuitry 1050 may control various aspects of the transducer elements and ultrasound transducers as disclosed herein. For example, transducer drive circuitry 1050 may provide a driving waveform for the ultrasound transducer. For example, transducer drive circuitry 1050 may provide a driving waveform for the excitation device. For example, transducer drive circuitry 1050 may receive a waveform from the transducer corresponding to the reflected ultrasound signal from the device.

Device 1000 may comprise a digital processing device 1090 as described elsewhere herein. For example, 1000 may comprise microprocessor 1092 which may control various aspects of the device 1000 including pneumatic driver 1071, pressure sensor 1073, optical drive 1063, optical source 1061, and transducer drive 150. Microprocessor 1092 may be connected to analog front end 1091 which may comprise an on-board PCB comprising connects for the various components. Digital processing device 1090 may connected to a display 1080 which may be visible to a user.

Figure 14:
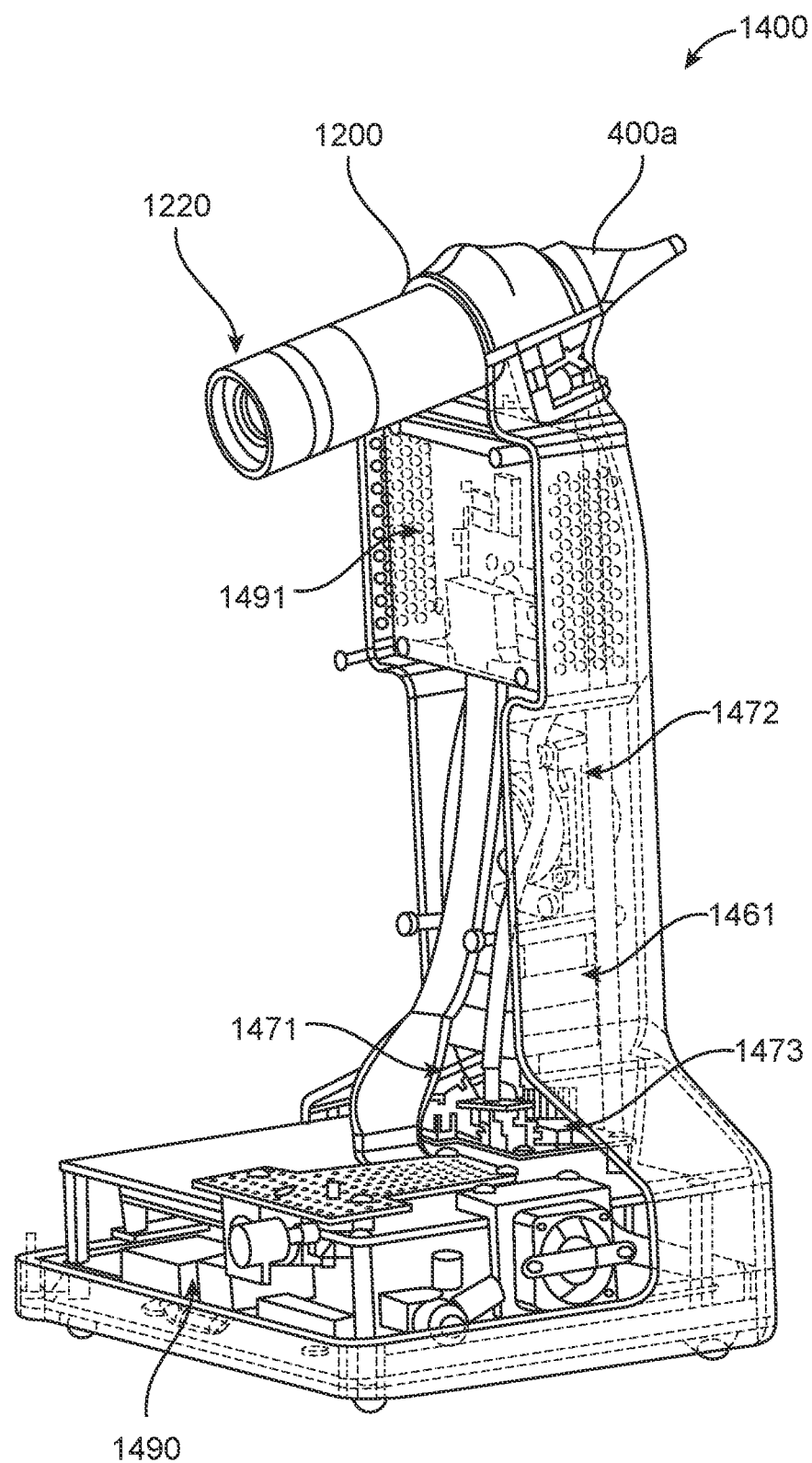
FIG. 14 is a transparent perspective view of an example device body which comprises an eyepiece, in accordance with some embodiments.

FIG. 14 illustrates a transparent perspective view of an example device body 1400 which may comprise an eyepiece, in accordance with some embodiments. A device 1400 may comprise interface 1200 as described herein above. Interface 1200 may comprise optical relay system 1220. Interface 1200 may be releasably connected to speculum 400*a*. Device 1400 may comprise various subsystems as described with respect to FIG. 10B.

Device 1400 may comprise pneumatic driver 1472 and associated drive circuitry 1471 within the body of the device. In some examples, a pneumatic driver may be an excitation generator. The excitation generator may be an air bladder manipulated by an operator to apply a force to a membrane or surface, an air displacement generator producing alternating pressure, step pressure, or air puffs. The excitation generator output may be a puff of gas such as atmospheric air or other suitable gas. In some examples, an excitation generator or a pneumatic driver is a voice coil actuator. In some examples, the excitation generator may produce a sonic excitation, a sub-sonic excitation, or a super-sonic excitation. For example, the excitation generator may produce a sub-audio frequency below 20 Hz, an audio frequency from 20 Hz to 20 kHz, or a super-audio frequency above 20 KHz. In an example, a sonic excitation, a sub-sonic excitation, or a super-sonic excitation may be produced by a piezoelectric transducer. The piezoelectric transducer may convert an electrical signal to a physical displacement which may in turn induce a pressure wave. In an example, a sonic excitation, a sub-sonic excitation, or a super-sonic excitation may be produced by a cMUT transducer. Device 1400 may comprise pressure sensor 1473. A pressure may be used to track a frequency and/or intensity of a pneumatic excitation.

Device 1400 may comprise an optical source 1461. An optical source may comprise an LED. An optical source may comprise a light bulb. An optical source may comprise an optic fiber which terminates outside of the housing and collects ambient light. Device 1400 may comprise driving circuitry for the optical assembly. Driving circuitry for the optical assembly may comprise motor controls for a movable lens and/or a display assembly.

Device 1400 may comprise transducer drive circuitry. In some cases, a transducer drive circuitry may be integrated with an on-board digital processing device 1490 or microprocessor 1491 as described herein. Transducer drive circuitry may control various aspects of the transducer elements and ultrasound transducers as disclosed herein. For example, transducer drive circuitry may provide a driving waveform for the ultrasound transducer. For example, transducer drive circuitry may provide a driving waveform for the excitation device. For example, transducer drive circuitry may receive a waveform from the transducer corresponding to the reflected ultrasound signal from the device.

Device 1400 may comprise a digital processing device 1490 as described elsewhere herein. For example, 1400 may comprise a microprocessor which may control various aspects of the device 1400. A microprocessor may be connected to analog front end 1491 which may comprise an on-board PCB comprising connects for the various components.

Figure 15A:
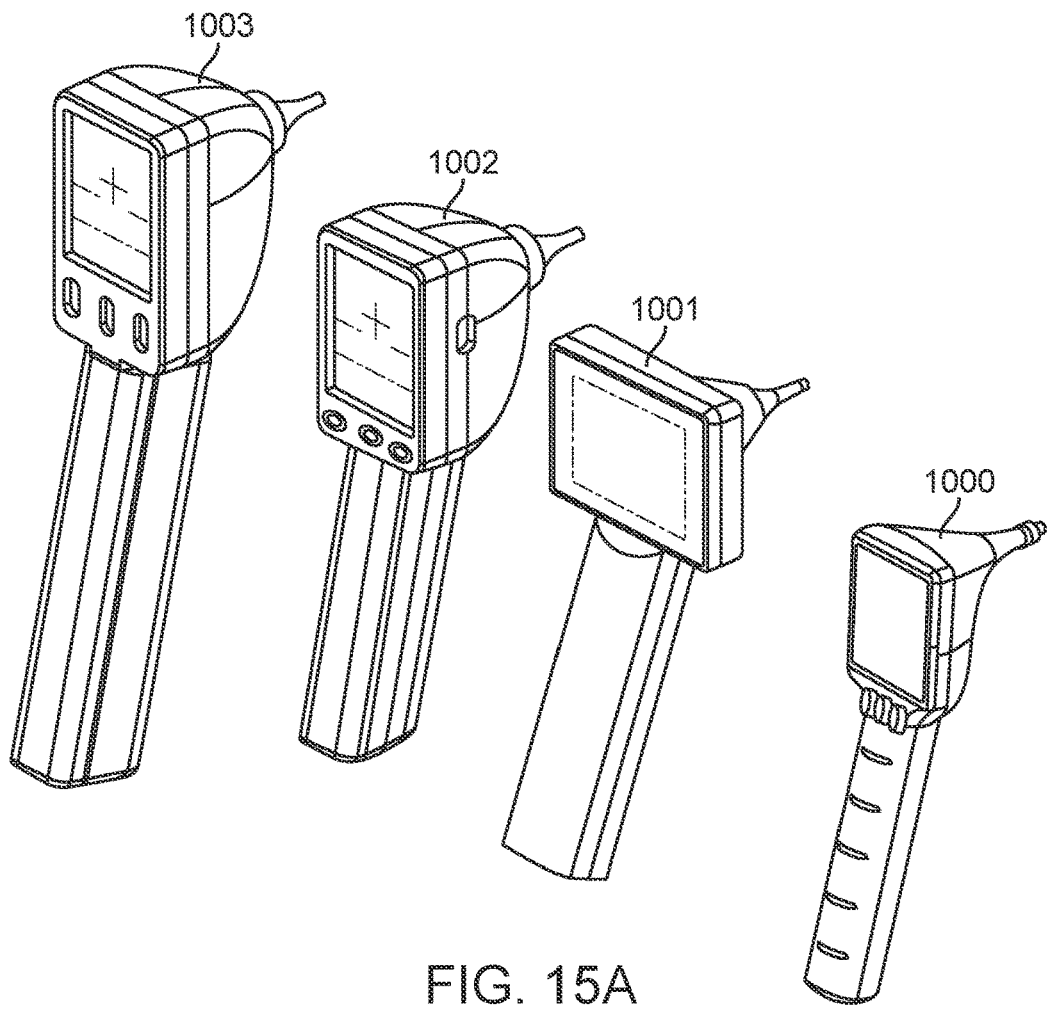
FIG. 15A and FIG. 15B show perspective and back views, respectively, of various example housings, in accordance with some embodiments.
Figure 15B:
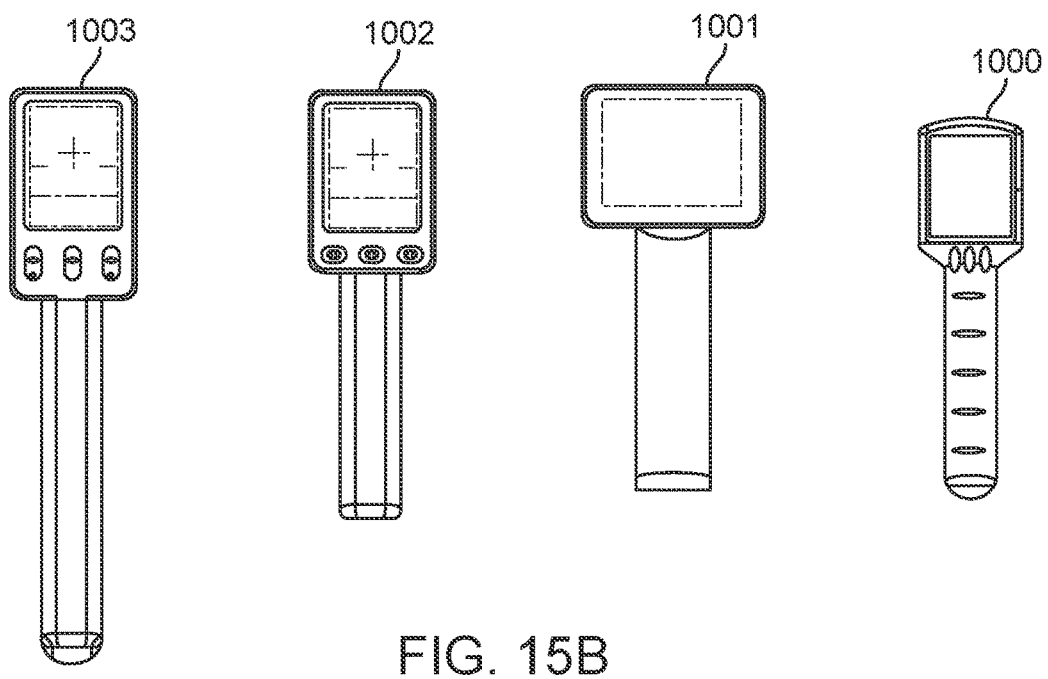

FIG. 15A and FIG. 15B show perspective and back views, respectively, of various examples of housings, in accordance with some embodiments. Device 1000 is shown as example devices 1001, 1002, and 1003. A device may comprise a screen which may display a live image of the target to a user. A screen may display a cross hairs or targeting aids. A screen may display live ultrasound data. A screen may display live optical data. A display may comprise one or more buttons. A display may comprise a touch screen. A housing may comprise a wide variety of profiles and shapes.

The devices, otoscopes, specula, and methods of use and manufacture thereof as disclosed herein may be used to characterize a surface. The surface may be biological membrane such as a tympanic membrane. A pneumatic excitation may change a response of a membrane to ultrasound excitation. For example, a pneumatic excitation may cause a membrane to deflect which may change a phase of the reflected ultrasound relative to a membrane that was not exposed to the pneumatic excitation. A deflection of the membrane may comprise a damped harmonic motion. This motion may be affected by changes in the elasticity of the membrane. A change in the membrane elasticity may occur, for example, if water, bacterial growth, or other foreign material is adjacent the membrane.

Surface characterization methods which may be applicable herein are also described in U.S. Patent Publication 2018/0310917 and U.S. Patent Publication 2017/0014053, each of which is incorporated by reference in their entireties.

In some examples, a pneumatic excitation may generate a movement of the surface or membrane during an interval of time. This interval may be coincident with acoustic wave delivered by an ultrasound transmitter to the surface or membrane. A pneumatic excitation may be continuous, may be pulsed, etc. The ultrasound reflected from the surface may be received at a transducer. A transducer may be the same transducer that generated the incident acoustic wave. A displacement of the surface or membrane may be related to a phase change in the received signal when compared to the transmit signal. A movement of the membrane may affect a phase change in the received ultrasound. A displacement may vary with time. An analysis of the temporal displacement of the surface or membrane, as measured by the phase shifts of the reflected ultrasound in response to the pneumatic excitation coupled to the surface or membrane may be used to determine the mechanical characteristics of the surface or membrane.

An analysis of the temporal information may be used in combination with the temporal displacement measured from templates of other membrane responses to create a comparison. An analysis of the temporal information may be used in combination with other metrics associated with the delay in an amplitude of reflected ultrasound, which characterizes the response of the surface or membrane. The mechanical characteristics measured may include ductility, elasticity, hardness, etc. A non-contact measurement of the mechanical properties a surface or alternatively a fluid below the surface of a membrane may be determined.

In some embodiments, an elasticity of a surface may be measured. The phase and/or amplitude of the reflected ultrasound from the membrane may be analyzed to produce an elasticity metric. The elasticity measurement may characterize a series of measurements in response to an applied excitation. The elasticity metric may be derived from the response of the surface and may provide an indication of one or more of several different phenomena. For example, the elasticity metric may indicate whether a surface adjacent to a membrane has a gaseous boundary or fluid boundary. For example, a membrane may move less, move more slowly, and or not move at all if the membrane has a fluid boundary. In an example, the elasticity metric may indicate, for the case of characterizing a fluid behind the membrane fluid boundary, the extent or a characteristic of the fluid. In some examples, the elasticity metric may be used to measure the characteristics of an elastic fluid with or without hysteresis of response. In a fluid with a hysteresis response, the fluid may exhibit an offset in displacement response, or "memory," such that the response behavior in one direction is similar to the response behavior in the opposite direction, but only after traveling a particular displacement distance. For a hysteresis response, it may be necessary to characterize the linear behavior of the response after a particular measured displacement associated with the hysteresis of the system. A fluid elasticity metric may be determined from the characteristic response of the surface or membrane to the surface excitation and reflected ultrasound characterization.

In some embodiments, a surface deflection may be estimated. For example, the estimate of surface deflection may be derived from a measured estimate of velocity, acceleration, or any other metric associated with deflection over time. For example, a displacement of the surface will result in a shortened path from the transducer to the surface, and the reflected signal from the surface back to the transducer will return with a phase shift. The phase shift of the reflected ultrasound relative to an excitation thus confers information about an amount of deflection. With an estimate of the force applied by the excitation, an estimate of the elasticity of the membrane can be estimated.

In an example, the excitation is a step or impulse response with a rising edge, falling edge, or impulsive excitation. The impulse excitation starts an oscillating deflection of the membrane. The reflected ultrasound can be measured from the time of excitation through the damping period of the oscillation of the membrane. In some embodiments, an estimate of elasticity or viscosity may be performed by examination of a ringdown characteristic. For example, the ringdown characteristic may comprise at least one of an exponential decay time or a ring cycle interval or frequency, such as the decomposition of a response into a ringdown characteristic, such as:

$$\phi(t) = e^{-t/\tau} \cos(2\pi f t)$$

where:
- $\phi(t)$ is the captured phase for a series of measurements;
- $\tau$ is the exponential decay coefficient;
- f is the ring cycle frequency; and
- t is time.

The damping constant of the oscillator may relate to energy lost from the membrane into the surrounding environment. In an example, if the membrane is adjacent to a fluid, the fluid may damp the oscillation of the membrane. The viscosity of the fluid may relate to the damping of the oscillator. The ring cycle frequency may relate to the restoring constant of the elastic membrane. The restoring constant may be related to the elasticity of the membrane. The restoring constant may be related to the viscosity of a fluid adjacent the membrane. The ring cycle frequency may be higher the lower the viscosity of a fluid adjacent the membrane.

Each excitation event may start a new deflection of the membrane. For example, an impulse excitation may pull the membrane in or push the membrane out for a limited period of time. For example, a square wave excitation may pull the membrane in or push the membrane out for a longer time. For example, a sine wave or other more complex excitation may be applied and the observed ringdown at the transducer may be a cross-correlation of the excitation field with the responding field.

Figure 19:
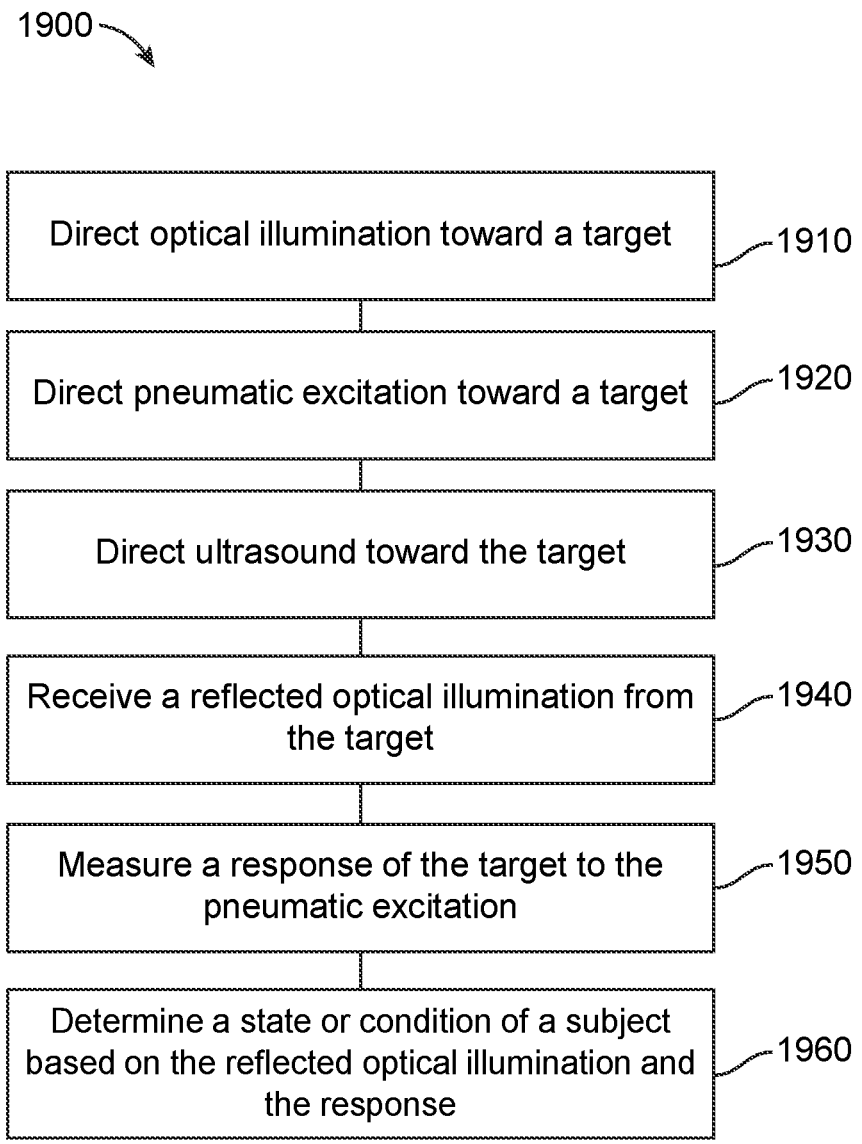
FIG. 19 is a flow chart of an example method of using an otoscope, in accordance with some embodiments.

FIG. 19 is a flow chart of an example method of using an otoscope, in accordance with some embodiments. At an operation 1910, a method 1900 for using an otoscope may comprise directing optical illumination toward a target. At an operation 1920, a method 1900 for using an otoscope may comprise directing pneumatic excitation toward the target. At an operation 1930, a method 1900 for using an otoscope may comprise directing ultrasound toward the target, wherein the ultrasonic is copropagating with the optical illumination. At an operation 1940, a method 1900 for using an otoscope may comprise receiving a reflected optical illumination from the target at a detector. At an operation 1950, a method 1900 for using an otoscope may comprise measuring a response of the target to the pneumatic excitation in the reflected ultrasound. At an operation 1960, a method 1900 for using an otoscope may comprise determining a state or condition of a subject based on the reflected optical illumination and the response.

An operation 1960 may comprise using one or more optical features of a membrane. For example, a membrane color, presence of visible fluid or a bubble behind a surface, visible effusion, visible inflammation, etc.

Although the above operations show a method 1900 of using an otoscope in accordance with some embodiments, a person of ordinary skill in the art will recognize many variations based on the teachings described herein. The steps may be completed in any order. Steps may be added or deleted. Some of the steps may comprise sub-steps. Many of the steps may be repeated as often as beneficial to the characterization of the surface.

One or more steps of the method 1900 may be performed with the circuitry as described herein, for example, one or more of the digital processing device or processor or logic circuitry such as the programmable array logic for a field programmable gate array. The circuitry may be programmed to provide one or more steps of the method 1900, and the program may comprise program instructions stored on a computer readable memory or programmed steps of the logic circuitry such as the programmable array logic or the field programmable gate array, for example.

Figure 20:
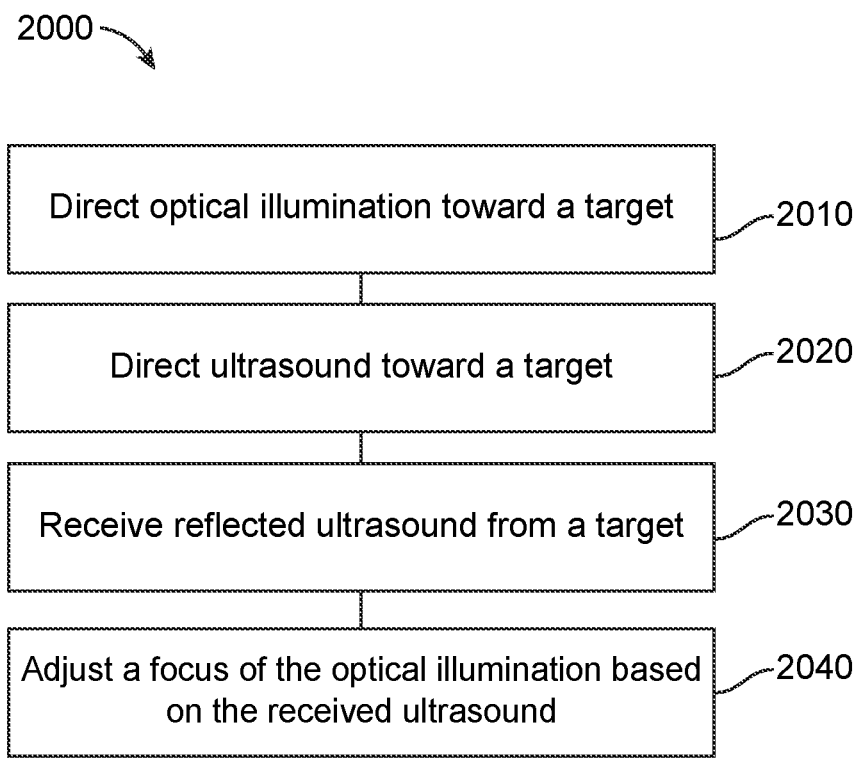
FIG. 20 is a flow chart of an example method of using an optical and ultrasonic device, in accordance with some embodiments.

FIG. 20. is a flow chart of an example method of using an optical and ultrasonic device, in accordance with some embodiments. At an operation 2010, a method 2000 for using an otoscope may comprise directing optical illumination toward a target. At an operation 2020, a method 2000 for using an otoscope may comprise directing ultrasound toward the target. At an operation 2030, a method 2000 for using an otoscope may comprise receiving reflected ultrasound from the target. At an operation 2040, a method 2000 for using an otoscope may comprise adjusting a focus of the optical illumination based on the received reflected ultrasound, wherein the adjusting is performed substantially in real time.

A method 2000, for example as illustrated in FIG. 20, may further comprise calculating an image crispness, calculating a derivative of the image crispness, and adjusting the focus based on the image crispness. The operation of adjusting a focus may comprise translating one or more mirrors. The operation of adjusting a focus may comprise translating a detector. Calculating an image crispness may comprise calculation of a gradient. Calculating an image crispness may comprise an edge finding algorithm. An image crispness may comprise a portion of a feed back loop for image focusing. A calculation of an image crispness may comprise calculation of a derivative followed by calculation of a square or a magnitude of the derivative. A calculation of a image crispness metric may comprise an average of derivative values and/or derivative magnitudes at edge boundaries.

Although the above operations show a method 2000 of using an optical and ultrasonic device in accordance with some embodiments, a person of ordinary skill in the art will recognize many variations based on the teachings described herein. The steps may be completed in any order. Steps may be added or deleted. Some of the steps may comprise sub-steps. Many of the steps may be repeated as often as beneficial to the characterization of a target.

One or more steps of the method 2000 may be performed with the circuitry as described herein, for example, one or more of the digital processing device or processor or logic circuitry such as the programmable array logic for a field programmable gate array. The circuitry may be programmed to provide one or more steps of the method 2000, and the program may comprise program instructions stored on a computer readable memory or programmed steps of the logic circuitry such as the programmable array logic or the field programmable gate array, for example.

Figure 17:
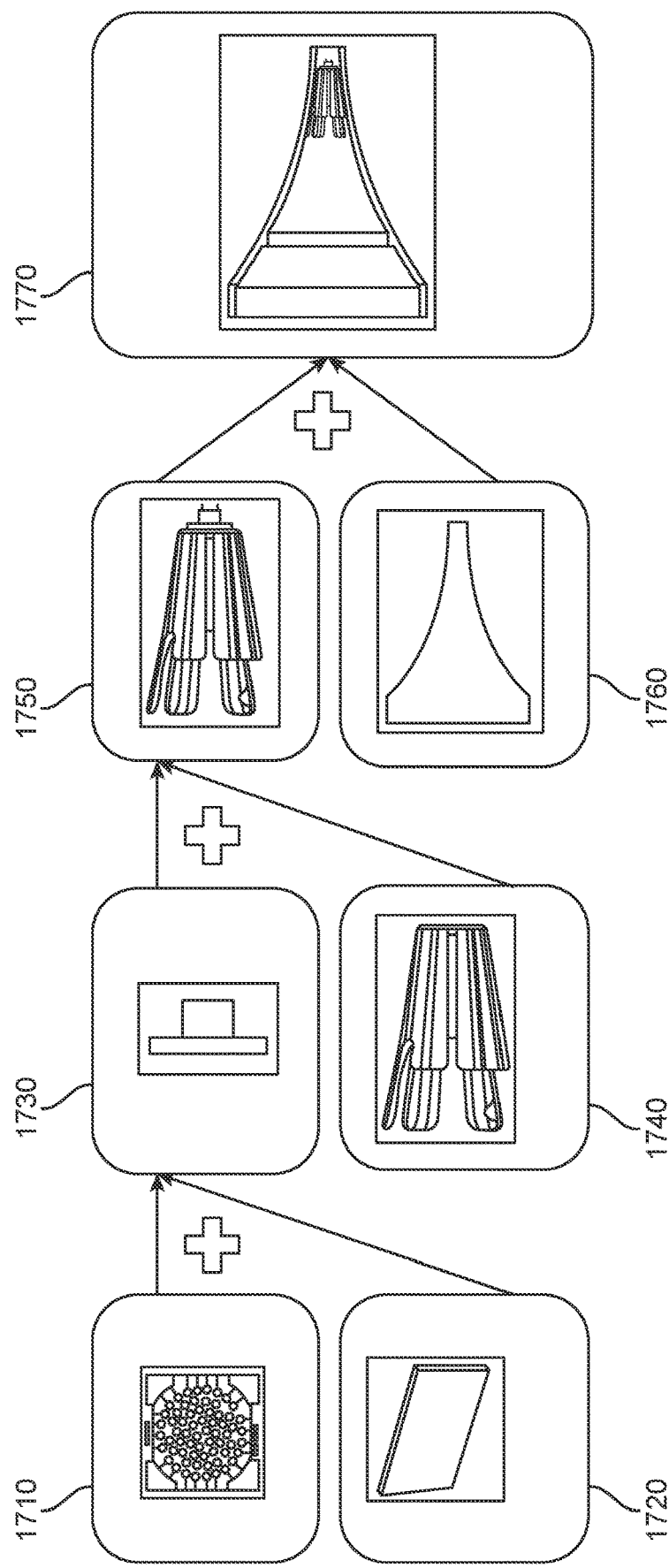
FIG. 17 is a flow chart of an example method of manufacturing a speculum, in accordance with some embodiments.

FIG. 17 is a flow chart of an example method of manufacturing a speculum, in accordance with some embodiments. Aspects of the present disclosure provide a method 1700 of manufacturing a speculum. The speculum may be disposable within an ear. An operation 1710 of the method may comprise providing a transducer. An operation 1720 may comprise providing a plate or substrate. An operation 1730 may comprise mounting a transducer on a plate or substrate. An operation 1740 may comprise providing a support. An operation 1750 may comprise mounting the plate or substrate on a support comprising an electrically conducting portion, wherein the support has a pneumatically clear path when the support is mounted. The support may be a transducer mount assembly as disclosed herein. An operation 1760 may comprise providing a speculum. An operation 1770 may comprise fitting the support within a lumen of the speculum, wherein the transducer is centered within the lumen of the speculum, wherein the speculum has an optically clear path when the transducer is within the lumen.

A method of manufacturing a speculum may comprise: mounting an ultrasound transducer on a substrate; mounting the substrate on a support comprising an electrically conducting portion, wherein the support has a pneumatically clear path when the support is mounted; and fitting the support within a lumen of the speculum, wherein the transducer is centered within the lumen of the speculum, wherein the speculum has an optically clear path when the transducer is within the lumen.

Although the above operations show a method 1700 of manufacturing a speculum in accordance with some embodiments, a person of ordinary skill in the art will recognize many variations based on the teachings described herein. The steps may be completed in any order. Steps may be added or deleted. Some of the steps may comprise sub-steps. Many of the steps may be repeated as often as beneficial to the method of manufacture.

One or more steps of the method 1700 may be performed with the circuitry as described herein, for example, one or more of the digital processing device or processor or logic circuitry such as the programmable array logic for a field programmable gate array. The circuitry may be programmed to provide one or more steps of the method 1700, and the program may comprise program instructions stored on a computer readable memory or programmed steps of the logic circuitry such as the programmable array logic or the field programmable gate array, for example.

In some embodiments, devices, specula, otoscopes, and methods of us and manufacture thereof described herein include a digital processing device or use of the same. For example, a digital processing device may be used to control various aspects of the devices and methods disclosed herein. For example, a digital processing device may adjust a position of one or more optical elements; may control the operation of a transducer such as analog to digital conversion of the received ultrasound signal, providing a waveform, etc; may process one or more images received at the detector; may provide instructions to a user to adjust a steering of the device; may control application of a pneumatic excitation; may measure a pressure with an biological lumen; may provide an indication of a quality of an air seal; etc.

A digital processing device may comprise an on-board microprocessor. In some cases, a digital processing device may be connected by wireless link to an on-board digital processing device.

Figure 18:
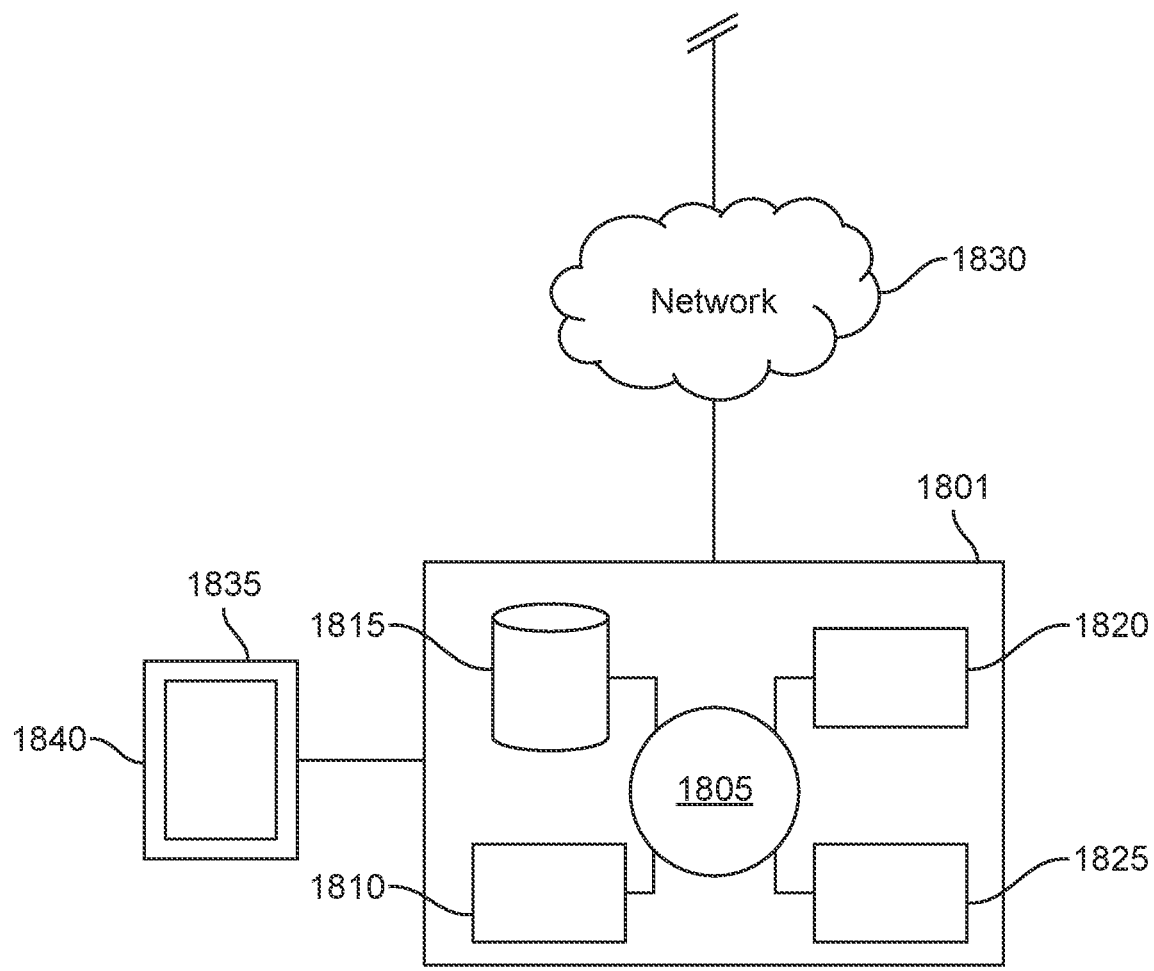
FIG. 18 is a schematic of an example system for measuring reflected ultrasound and optical signal comprising a digital processing device and a display visible to a user, in accordance with some embodiments.

Digital processing devices 1090 and 1490 may comprise embodiments, variations, or examples of the digital processing devices disclosed herein including, for example, device 1801 in FIG. 18.

In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device may be optionally connected a computer network. In further embodiments, the digital processing device is optionally connected to the internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Referring to FIG. 18, in a particular embodiment, an example digital processing device 1801 is programmed or otherwise configured control to an imaging component and/or instruments as described herein. The device 1801 may regulate various aspects of the imaging component and/or instruments of the present disclosure, such as, for example, performing processing steps. In this embodiment, the digital processing device 1801 includes a central processing unit (CPU, also "processor" and "computer processor" herein) 1805, which may be a single core or multi core processor, or a plurality of processors for parallel processing. The digital processing device 1801 also includes memory or memory location 1810 (e.g., random-access memory, read-only memory, flash memory), electronic storage unit 1815 (e.g., hard disk), communication interface 1820 (e.g., network adapter) for communicating with one or more other systems, and peripheral devices 1825, such as cache, other memory, data storage and/or electronic display adapters. The memory 1810, storage unit 1815, interface 1820 and peripheral devices 1825 are in communication with the CPU 1805 through a communication bus (solid lines), such as a motherboard. The storage unit 1815 may be a data storage unit (or data repository) for storing data. The digital processing device 1801 can be operatively coupled to a computer network ("network") 1830 with the aid of the communication interface 1820. The network 1830 can be the Internet, an internet and/or extranet, or an intranet and/or extranet that is in communication with the Internet. The network 1830 in some cases is a telecommunication and/or data network. The network 1830 can include one or more computer servers, which can enable distributed computing, such as cloud computing. The network 1830, in some cases with the aid of the device 1801, can implement a peer-to-peer network, which may enable devices coupled to the device 1801 to behave as a client or a server.

Continuing to refer to FIG. 18, the CPU 1805 can execute a sequence of machine-readable instructions, which can be embodied in a program or software. The instructions may be stored in a memory location, such as the memory 1810. The instructions can be directed to the CPU 1805, which can subsequently program or otherwise configure the CPU 1805 to implement methods of the present disclosure. Examples of operations performed by the CPU 1805 can include fetch, decode, execute, and write back. The CPU 1805 can be part of a circuit, such as an integrated circuit. One or more other components of the device 1801 can be included in the circuit. In some cases, the circuit is an application specific integrated circuit (ASIC) or a field programmable gate array (FPGA).

Continuing to refer to FIG. 18, the storage unit 1815 can store files, such as drivers, libraries and saved programs. The storage unit 1815 can store user data, e.g., user preferences and user programs. The digital processing device 1801 in some cases can include one or more additional data storage units that are external, such as located on a remote server that is in communication through an intranet or the Internet. The digital processing device 1801 can communicate with one or more remote computer systems through the network 1830. For instance, the device 1801 can communicate with a remote computer system of a user.

Examples of remote computer systems include personal computers (e.g., portable PC), slate or tablet PCs (e.g., Apple® iPad, Samsung® Galaxy Tab), telephones, Smart phones (e.g., Apple® iphone, Android-enabled device, Blackberry®), or personal digital assistants.

Methods as described herein can be implemented by way of machine (e.g., computer processor) executable code stored on an electronic storage location of the digital processing device 1801, such as, for example, on the memory 1810 or electronic storage unit 1815. The machine executable or machine-readable code can be provided in the form of software. During use, the code can be executed by the processor 1805. In some cases, the code can be retrieved from the storage unit 1815 and stored on the memory 1810 for ready access by the processor 1805. In some situations, the electronic storage unit 1815 can be precluded, and machine-executable instructions are stored on memory 1810.

The digital processing device 1801 can include or be in communication with an electronic display 1835 that comprises a user interface (UI) 1840. Examples of UI's include, without limitation, a graphical user interface (GUI) and web-based user interface. In some cases, electronic display 1835 may be connected to the computer system 1801 via a network, e.g., via network 1830.

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the embodiments of the present disclosure. It is intended that the following claims define the scope of invention and that methods and structures within the scope of these claims and their equivalents be covered thereby.

What is claimed is:

1. A speculum operable to be disposed within an ear of a subject, the speculum comprising:
    a housing configured to be coupled to a handle, wherein the housing comprises a lumen, wherein the lumen is configured to receive reflected optical illumination from the tympanic membrane and to transmit a pneumatic excitation to the tympanic membrane;
    an ultrasound transducer mounted within the lumen, centered relative to a distal end of the housing, and disposed between a distal end and a proximal end of the housing; and
    a transducer mount assembly upon which the ultrasound transducer is mounted, wherein the transducer mount assembly comprises one or more apertures configured to allow transmission of a pneumatic excitation around the ultrasound transducer and an optically transparent region configured to allow transmission of the reflected optical illumination in an annular region around the ultrasound transducer, and wherein the reflected optical illumination is directed toward a detector configured to receive the reflected optical illumination.

2. The speculum of claim 1, wherein the detector is configured to measure a response of a tympanic membrane to the pneumatic excitation.

3. The speculum of claim 2, further comprising a processor configured to determine a condition of the tympanic membrane based on the response of the tympanic membrane to the pneumatic excitation.

4. The speculum of claim 1, wherein the optical source further comprises a light guide.

5. The speculum of claim 1, wherein a transmission axis of the ultrasound transducer is coaxial with an axis of symmetry of the housing.

6. The speculum of claim 1, wherein a transmission axis of the ultrasound transducer is coaxial with an optical path of the optical source.

7. The speculum of claim 1, wherein a largest dimension of the lumen is a diameter, and wherein the diameter is within a range within 20% to 60% of a smallest diameter of the lumen.

8. The speculum of claim 1, wherein the speculum is disposable.

9. The speculum of claim 1, wherein the speculum is removably attachable to an otoscope comprising an optical assembly, wherein the optical assembly comprises at least one lens configured to focus the reflected optical illumination from the tympanic membrane onto a detector.

10. The speculum of claim 9, wherein the speculum when connected to the otoscope is axially aligned with a focal axis of an optical assembly.

11. The speculum of claim 9, wherein the optical assembly comprises a focus within a range from 12-25 mm from a distal tip of the otoscope.

12. The speculum of claim 9, wherein the optical assembly comprises a depth of field of greater than 0.5 mm at a distance 12-25 mm from the distal tip of the otoscope.

13. The speculum of claim 1, wherein a distal end of the transducer mount assembly is operably coupled to a transparent plate and wherein the transparent plate comprises the ultrasound transducer mounted on a surface thereof.

14. The speculum of claim 1, wherein a metal shield is disposed around the ultrasound transducer, wherein the metal shield is radially displaced away from a transmission axis of the ultrasound transducer.

15. The speculum of claim 9, wherein the otoscope further comprises an optical source, wherein the optical source comprises a laser.

16. A method of using an otoscope, the method comprising:
    directing an optical illumination toward a target via the otoscope, wherein the optical illumination is reflected off the target as a reflected optical illumination;
    directing a pneumatic excitation toward the target via the otoscope, wherein the pneumatic excitation is directed by transmission through one or more apertures of a transducer mount assembly upon which an ultrasound transducer is mounted;
    transmitting the reflected optical illumination in an annular region around the ultrasound transducer through an optically transparent region of the transducer mount assembly;
    receiving the reflected optical illumination from the target at a detector;
    measuring a response of the target to the pneumatic excitation with the ultrasound transducer; and
    determining a state or condition of a subject based on one or more of the reflected optical illumination or the measured response.

17. The method of claim 16, wherein the optical illumination is directed from a laser.

18. The method of claim 16, wherein the target is a tympanic membrane.

19. The method of claim 18, further comprising characterizing a surface of the tympanic membrane by analyzing the measured response.

20. The method of claim 18, further comprising displaying activity of the tympanic membrane in a display of an otoscope.

21. The method of claim 19, further comprising capturing activity of the tympanic membrane in real-time and displaying, on a display coupled to the otoscope, the real-time activity.

22. The method of claim 19, further comprising recording the response of the tympanic membrane to the pneumatic excitation.

23. The method of claim 16, further comprising directing an ultrasound signal toward the target via the ultrasound transducer.

24. The method of claim 23, wherein the ultrasound signal copropagates with the optical illumination.

25. The method of claim 23, wherein the ultrasound signal is reflected off the target as a reflected ultrasound signal, and wherein a response of the target to the pneumatic excitation in the reflected ultrasound signal is measured.

26. The method of claim 16, further comprising measuring an internal pressure within the otoscope.

27. The speculum of claim 9, wherein the otoscope further comprises a pressure gauge configured to measure an internal pressure within the speculum.

\* \* \* \* \*